United States Patent
Chen et al.

(10) Patent No.: US 11,499,139 B2
(45) Date of Patent: Nov. 15, 2022

(54) TARGETED INTEGRATION SITES IN CHINESE HAMSTER OVARY CELL GENOME

(71) Applicant: DEVELOPMENT CENTER FOR BIOTECHNOLOGY, New Taipei (TW)

(72) Inventors: Hsuan-Pu Chen, New Taipei (TW); Hsin-Lin Lu, New Taipei (TW); Chien-I Lin, New Taipei (TW); Hsueh-Lin Lu, New Taipei (TW); Tao-Tien Chen, New Taipei (TW)

(73) Assignee: DEVELOPMENT CENTER FOR BIOTECHNOLOGY, New Tapei (TW)

( * ) Notice: Subject to any disclaimer, the term of this patent is extended or adjusted under 35 U.S.C. 154(b) by 818 days.

(21) Appl. No.: 16/472,108

(22) PCT Filed: Dec. 19, 2017

(86) PCT No.: PCT/US2017/067283
§ 371 (c)(1),
(2) Date: Jun. 20, 2019

(87) PCT Pub. No.: WO2018/118901
PCT Pub. Date: Jun. 28, 2018

(65) Prior Publication Data
US 2020/0157509 A1 May 21, 2020

Related U.S. Application Data

(60) Provisional application No. 62/436,714, filed on Dec. 20, 2016.

(51) Int. Cl.
*C12N 5/071* (2010.01)
*C12N 15/85* (2006.01)
*C12N 15/90* (2006.01)

(52) U.S. Cl.
CPC .......... *C12N 5/0682* (2013.01); *C12N 15/85* (2013.01); *C12N 15/907* (2013.01)

(58) Field of Classification Search
None
See application file for complete search history.

(56) References Cited

U.S. PATENT DOCUMENTS

| | | |
|---|---|---|
| 2002/0055172 A1 | 5/2002 | Harrington |
| 2013/0302815 A1 | 11/2013 | Van De Water et al. |
| 2016/0115502 A1 | 4/2016 | Shen et al. |
| 2016/0145645 A1 | 5/2016 | Bahr et al. |

OTHER PUBLICATIONS

Hamaker et al. "Site-specific intergration ushers in a new era of precise CHO cell line engineering" 22 Current Opinion in Chemical Engineering 152-160 (Year: 2018).*

Jae Seong Lee et al., "Accelerated homology-directed Targeted Integration of Transgenes in Chinese Hamster Ovary Cells Via CRISPR/Cas9 and Fluorescent Enrichment", Biotechnology and Bioengineering, Nov. 2016, pp. 2518-2523, vol. 113, No. 11, Wiley Periodicals, Inc.

Jae Seong Lee et al., "Site-specific Integration in CHO cells mediated by CRISPR/Cas9 and homology-directed DNA repair pathway", Scientific Reports, 5:8572, Feb. 25, 2015, pp. 1-11.

Simon Fischer et al., "The art of CHO cell engineering: A comprehensive retrospect and future perspectives", Biotechnology Advances, 33, Dec. 2015, pp. 1878-1896.

* cited by examiner

*Primary Examiner* — Nancy J Leith
(74) *Attorney, Agent, or Firm* — Muncy, Geissler, Olds & Lowe, P.C.

(57) ABSTRACT

Described herein are specific CHO genomic sites for targeted insertion of exogenous genes. The sites are located within a sequence selected from SEQ ID NOs: 1-16.

25 Claims, 7 Drawing Sheets
Specification includes a Sequence Listing.

```
CTTCCAAGTAAATATCCACAACTACACGGTTCATGAGATTACTCGCAGGATTTAGGATTTTAAAGAATAATAGTAAACA
GAAGCAAGGAAGTGATCGGGTTTGAGGAGGTCACACCTCTTTAATGCACTTAAAGAGGACAGGAATACAGTCCCAGCTG
AAGTCCAAGAGAAGACAGACAAAGGGAAGGGCGCACTTAATACAGAGGAATAAATACTGAAGGGAGCTCGGGCTGAAAT
GGAGCTAGAACTGAAAAATTCAATATCCCATCTGTTAGGGTCACCGGAGGACAGGACACCAGACACCTTCAGGCAAACA
GCTTTTATATGTGAGAGGAGTCATGAGAGAACCAGACCAGAGCCTAGCCAGACAGACACCTGTTCCGTACCATAGTCT
AACCGCTGCTTTAAACACAGTGTGGGCTTAAATGTCTTTCATGTCAGGAAGGGAGGACGGCTTGGGAGCATTGCCAGGC
CACACATAACACTTTGGTGGAGACTAAACAGGATGGTGGTCTCTTTGTCCTTCTTTCAAGGCCTCCTGGAAGATTTACT
AAGGAAAGGGGATTACTGGGGAGATGTATCAAGGTTTTTATACACGCAAGGGCATTGCTCGGCCCTGTGGCTGCATCTG
GTTTTCATTGCCCTGGCTCTCAAGGGAGTCTCCCTCACATAGGGTCAAGCAGGAGATAGGATGTCAGGACCGGGAGACA
CAGCAGAGAAACTGGAGAACAATATCTTTAAATCAAAGAAAGAAAAATATTTAAAAGGAATATGCAAGAATTTGGGGA
CACCATGAGGCCCAAACTTATGAGTTACCCGAGAAGACTCTCAGGTGGAAGAAAATGAATGGGGTATCCAGAGAAGACC
CATGGTTGCAATGCTTGTCTTAGTGTGTGAACCACACTCCAGCAGTCCACAATCTCTTGACCAACTCTCAAATGCCATCA
TCTGTTGAATATTCCCAGGAATTGGTCCATGAGTTCCCTGAAATCCCTCAAGATCTGATAATGCTCACCAGACCCGTCC
TCACAGACACTCACGAGATATGCTCCACTAATTTCCCAGGTATTTCCTAATCTTAGCACGTTGACAATCAAGGCTGAGC
ATCCCAACAGCATAAAGTTGACCAAGGAGCACGGGAAAAGTTGCACAGCATCGCTACTCATCCTGAGGATTAAAGTGAA
AACACCACGAGGAAAGATTCCTGGTTTGTCGCTTTGCTTGAACGAGCCTGGAAGTTTGCAGCTCATCCTCACACAGACA
CCCTGGTGAACCAACTAGAAACCTAGCAGTTCTCCTAGGCTGTGCAAGAAAGGTGAGCACACACAGGAGGAAATACATA
AAGAGACTGGAGTTCAGCGTTGAAGTCAGTAGGTCACAGGCACCCTGGGTCCTTGTCACACTTGCCTGACCCTGACCCC
GCCGGCACAAGAGGGTCTGGTTCTGCGGTTCCTTTACTCGCAGCAATTGAGTCTGGTTCCCAAGAAGACGCCCCACGCA
GGACGAGGAGACCCAGCGGGTTGGAAGGAATCCACGGCCGGAGGTGCGGGAGTGTTTCCCGGGGTGACCAGCAGGGGC
GCGGGGCGGGAAAGCCTTCGGGGCTCCTGAAGTTGGGGTTCCCGGAATGAGGGGAGTGTGTGAGCCGGGCGGGCTGA
GAGCAGGTTAGAGCCAGGCCGAGAGCGGTTGGGGAGAAGGCGAACTGGGCGTGGTAGTTTTCACTCTACACTCCGCCCA
CAGTGTTGGGAGGGCGAGTACGTCATCGTAACTCAGCGCCTAACTAACGGTTTGATGTGAGCTGCTTCCGCCGGCTCTGG
TGGCGCAGGCCGGAAGGATTTGCTGAAGGAGGCAGAGGCAGGGGATCTGGAGTTCGAGGCCAGCCAGGACTACACATT
TTTTTTTCTTGTCCTCCAACAAAACATCCACAGCTACAGGCTACAGTAAAATTCCTACACCCACAAAGGCTCTCCACAC
TCTACTCTCAACCTCATTTCGCTCGCGACTGACACCCAACCGACACCATCTTTTCTAGACGCACAGGCGCCTGCTCCAC
CCTGCTGCTCACAAGCCTTTGCTCACACACCGACTCACACGCTCCACCTCCGCGCTGGCCAATGCTCGCATAGTCTAAC
GGCTACTTGAAACCCATAGTGTGGACTTAAATGTCTTTTACGTCAGGAAGGGTGGACGGCTTGGGAGCATTGCCAGGCC
ACACATAACACTTTGGTGGAGACTAAACAGGATGGTGGTCTCTTTGTCCTTCTTTCAAGGCCTCCTGGAAGACTTACTA
AGCAAAGCGGGGATTGCTGGGGAGATGTATCAAGGTTTCGATACACGCAAGGGCATTGCTCGGCCCTGTGGCTGCATC
TGGTTTTCATTGCCCTGGCTCTCAAGGGAGTCTCCCTCTCATTGAGAAGACTCAGTGGAAAGCCTTXXXXTGAXXX
XXXXXXAAGACAGAATGTCAGGACCTGCAGACACAGCAGAGCAACTGGGAAACAATACCTTAAAAACAAACAAA
GAAAAATATTTAAAAGGAATATGCAXXXXXXXXXXXXXXXXXXXCCCAAATTTATGAGTTAGCTGAGAAGACTG
TGGGGTGGAAGAAAATGAATGCGGTATCCAGAGAAGACCCATGGTTGCAAAGCTTGACCAGCTCTCAAATGCCATCATC
TGTTGAATATTCCCAGGAATTGGTCCATGCGTTCCCTGAAAACCCTCAAGATCTGATAATGCTCACCAGACCCGTCCTC
ACAGACACTCACGAGATATGCTCCACTAATTTCCCAGGTATTTCCTAATCTTAGCACGTTGACAATCAAGGCTGAGCAT
CCCAACAGCACAAAGTTGACCAAGGAGCACGGGAAAAGTTGCACAGCATCGCTACTCATCATGAGGATTAAAGTGAAAA
CACCACGAGGAAAGACTCCTGGTTTCTAGTTTTGCATGAAGGAGCCTGGAAGTTTGCAGCTCATCCTCACACAGACACC
CTGGTGAACCTACTAGAAACCTGACAGTTCTCATAGGCTGTGCAAGAAAGGTGAGCACACACAGGAGGAAATACATAGA
GAGACTGGAGTTCAGCGTTGAATTGTCCTCCAACAAAACATCCACAGCTACACACTACACTAAAATTCCTACACCCACA
AAGGCTCTCCGCACTCTACTTTCAACCTCGTTTCGCTCGCGACCGACACCCAACCGACACCATCTTCTTCAGACATAAT
GACTGTCAGTGTACAAATTAAATGAATTATTTACTAGGAGCTGAAAGACCATTGCAACTGCTCGCCAATTCGACTATTT
GAGCTGAAGCCGGAGTTGTCTGCTCCACATATTTCTTTCCATCAATAATATAGGCGGCTCTCCCATTGGAGGAGCCATC
AGTAAAAACTAACATAGCATTTTTTACAGGATTGCTTTTAACAATTTTTGGAAATATAAAAGGATGCATTAGTGTAAAT
TGCAACAGTCCATGAGCTGGAAACTGAATATCAATTCTCCCTAAAAACTGATCAAAAGCAATCGCCCATGAATCACTGT
TTTGGAACAACCCATTAACCTGATGCTTGGTGTAAGGGACATGTATTATATTTGGCTCTTTGCCAAAATACTTCCTAGC
TTTTACAAGGCATTTTTGTACCATGCAGGCTACTGCTTCAAAATAAGGGTCTAATACTTTGGATGGCGAGACTGGTAGG
TGTAGCCACAGTATGGTCCCTCCTGCCACAGAACAGAAGTCGGACTATGCCTTGTGGGGAGTATATAAGCCTCCCATG
GCTTTGCATAGTCAATATAACATATTTGTTGACGCTGAATCGCCTCCTCCAATTGTAGCAGGACTCGTCTACCTTCCTC
TGTTAGCTTTCTAGGTGAATTGGATCATTATCTCCCTTTAAAATATCACAGAGCGGTTTCAAATCACCAGTAGGCTCT
CTTTAAAAAGCGACGTAACCATTGAATATTCCCTATTAATTTTTGAAAGTCATTTAAGGACCGTAAGCTATCTTTTTAA
TCTCTAATTTCTGAGGTCTAATCTCTTTAGCATATAACATATGACCCAAATATTGAAAAGGTGGCTGTCTCTGTACCTT
CTCTGGAGCACTCACTAAGCCTGCTCTCTTGAGACTTTGCTGTAGCTGTCCATAAATCTCGAGCAGAACCGCTTCATAT
TTATGGACAAGTAAAATATCATCTATATAATGAACAATAAAGACTTGTGGAAATCTGTCCCTAACCATTTGTATAGCTC
GAGACACAAACTTTTGGCATAAAGTTGCACTATTGGCCATGCCCTGGGGTAAAACCTTCCAATGGTACCTCCTCATGGC
TCTTTAAAATTAACTGAAGGAATGCTAAATGCAAACCTATGACAGTCCTGAGGAACCAGGGGAATAGTATAAAAACAAT
CTTTTAGGTCTACAACAATCTTATAAGTACCCTTTGGTACAGCTGCAGGAATGGGTAATCCTGGCTGTAGTGCTCCCAT
TGGCTGCATGGTTTTATTAACTTTCCTCAAATCTTGT
```

FIG. 1

CTGAGGACCAAGCAGGAGGAAAATCACAATAACATTCTTGAATAAAACAACCCTATTCCTAACCCTTTGGAAAGC
TGCCAGTTTGCTTAGAAGATAAGCACATGTCCCCCTCTCCCTCTAACACATTCACGTTCGGACGGAAGAGGGAGC
CCCATTCCCGAGTAGCACCCAACACTGAATGATCAATATGTCAGAAAAGGCCTGGTCCAAGGTTGTCCATAGGAA
CTAAATGCATCATAGCCAAAGCTTGCCAATGGCCCTGGTGCCTAACAGGCAGATACACAACTTTAGGCTTCTAG
ACAGAAGAACACCCAGTATCAAAACGAACCAGCTGCCACAGACTTGAACTAGAGGGAGCAAGCTCAGAACTACGG
GAGAGCAGCCAGATACATCGGCACACACAGAATGAGTACTCCCTGTATGAGATTCTGATGCCATTTGTGGGAAC
TTTGGAAAAGAGTAAGAAAAAGCTCAGTGTCAGACATTTTACAAGCATACTCTGGCTGTGGCCCCAACTGAAG
GGAAAAGACAGAAGAAACTATGACATGATTACCCCTCTCTAACACCCACCGGCAGCCAGACCCAGTGAAACCCTT
TGCAAGCTTGCAGGGAATGTCGGGAATTCTTGGCCGGGTGAGGGGGTGGGGGTGCATTATCTTAATGTGAACAG
CAGTCCTGGTGGTGGTTCCCTAGCCATGTTCCCGCCCCGTCTGTCCCACTGGATTTAAGCCTTACAGTAGGAGAC
AAGCCCATGCCTCCACATAGAGGTGGAGCCTGTTCCTTACAGTTCTACAACAGGGGACACCACCCACGGGGAAGG
AAACACAGAAGGCAGTTGTCA<ins>CTTCTACAGGTGTTTGTCATCAGGGCTTTAACCTGTACACCTACTTGGCACTTG</ins>
TCCTATGCTATTCATGTTGAAGTCCTAACTCCTAAGACTTCAGAATGTGACTATCTGGATACAGCCTTTTGTTTA
TTTTATTTTTGGTGTTTTGAGACAGGGTCGCACCACACAGCTTGGGCTGGCCTCAAACTCACAGAGATCCGCCTG
CCTCTGCCTCCGGAGAGCTGGGATTAAAGGCGTGCGCCGCCACCACACCTGGCTCCTGGGTATATATATATTCTT
AACGAGTTAAAACGGGGTCCTTAGGGTGGACCCGAACTCAAAGAGGTTGGTGTTTTTATGAGATGAGGACTCAGA
CACCCCATGTAGTTTCCATCTGCAGATCAAGGAAGATGAGAGGCCTGCAGAGAACCCAACGCCTTAATCTGAGGC
TGTGCCTTTGTAATTACAGATCCCCTAATTGGCCTTCTCCCTTTCCGAACTCGGGAACGCAAACTCAAGTACTGG
GACTGGGGGTGAGGGGGTGTGTGTCTCAAAATCTGGAGAATGCTGAGCATGCGCCAGGCCTCCCTCGCACCGTGA
TGAGCGCAAAACTCAA<ins>TGCACCTCAACAAGTCGCCC</ins>TAGGTTCAGATAGAGTGTGGAAAGAATACAGGACTCAG
GAGGCCCTCGGCACCGCTGCTGTGCCGACTGTGTCACCGCGTTAGGAGCCGCCCAGCCAGGCAGTGCCAGCGGT
AAACGCTCACCCAAGCTCGGGCTCACGGACGCAGGAGGACCCGCAGGGAGAGATGGGTGCCGGCACCCACCCTGCT
GCTGCCGACTCGTCCCCGGGAAGACCACCCATCACAGTTGCTAAGCGACGCGGGAGACTTTGTGCCGCGCAGGCT
TACACAGAGCCCCGGCGCGTAAGCCCCGCCCCTGGGTAGCCTCCCGCTGGTTTCCCGCGCCACACCCTCCAGAGC
<ins>CCC</ins>CGCCTCTTAATCCTCGGCCTATCCCGAGTCGTCTCGCGCACTACCCCCGCCCACCTCCAACTCTCGGCCTAT
CCCGCGCCGCGCCACGCGAAGACCCGCCCCTCCTTGCCATCCCTTTGGCCTTTCCGCGCCCCCTGAGTTCCACC
CACTTCCTCCCTCAGCCTATTGCGCGCCCTTGAGCCCCGCCCCGGCCTCTCCCGGCCTATCGCGCTCCGCCC
GTCGCCAGCCCGCCCCGCCGGCGTTGTGAGCGCGCTGTGACGTCCGCGCCGCTGTGGTCAGTGTTTGGTACCC
GCTGCCATGCCGAAGCGGAGCTGCCCGTTCGGGACGCTTCCCCGCTGCAGCTCAAGGTCCATGTGGGCCCGAGA
GAGCTGAGCCGCGGGTGTTCGCCAGCGCTACTCGCGGGAGGTCTTCGGTGAGTGCGGAGTTCCGTGGTAGGGC
GCGCAGCGCCGCGCCGTGGGAGACCCCAACTGGCTTGCGCGTCGCCATCCCCGGGGGGGAGGCGGCGTGGGGGG
GGTCCCCGGGGAGCGGCTCCGGGGGAAATGCGAGTGTAGCCGAGGACTGTCGAGCGGGAGTCGGCCCCCTCAAGT
GGGCTTTCTGGCGGC<ins>AGGGTGTTGCTTTGCAGTGATGG</ins>CTCTCTGGGGCCGATGCAACGCGGCTTACCTGGCTTA
GGGCGAAGTTTATGCCTGTAGTTTTGAGTGGTGCGCTGTGCCTTTGGGATGTGTCGTTAAAGCCCAGGCTGCGGA
ATTACAGACTCCCTAATGCGCCGTGTGTGTGTGTGTGTGTGTGTGTGTGTGTGTGTGTGTAGCTGATGGGC
CCTTTCCCTTTCTGTACTGTGGAATGCAAACTCGAGTGCTGAGACCTCAGGGGTGATGAGTGAAGTGTGAGGCCT
GAACAGCAAAGCGTCATGCACTCATTTAAAAGAAACAAAAGTAGACATGACGGGAGTCTTGGCATTCGCCCTTGA
TGCTAGCAACTCACCAGGCAGAAGCAGGCGGATCTCTGAGAGTTCCGGGGCCAGCCTGGTCTACAGAGCGAGTGC
CAGGACAGCCTCCAAAGCCACAGAGAAACCCTGTCTTGAACCACCCCACCCCCCAAAAAAAAGAAAACCTAAGT
ATAATTGGAACCTAGCAGCCTGGCTCTACTCTTTTAAAGACTTATATCCTGGAGCACTTGCCAGGGCCAGTCAGA
ACCAGCCAGGTCA<ins>GGGAGGGGTGCTGGTTTCTGG</ins>GGTGTTGTATAGTCATACAGTACACACAATTTGAGGCCTGA
AGGATGAATACCAAGCCTCGGCCTACACTCTGGACTCTTTTGTGGGCCAGGAGTCCTTGAGGAGAAAGATTACTC
TCAACATGGAATCTTCCTATCTCCCTCTTTTCAAGCAGGCTTTTACAATGTATCTTAGGCTAACCTTGAACTT
AAACACTCCTGCTGCCTCAGCCTCCTGAGTGCTGGGATGTGCCTCTGTATCTACTTTCTATCTAAAGCAGGAGG
TGGCACAGACTGTAACTGGCCTGATAACAGCCCACTCCCTGTGACTTTTTGCTGGCTGTTGCTGCTGCCAGTTTCA
CAGAGGGGCCCCTGGGTCTGACAGGTCTCCCCTGGCTCTGTATGTGGAGTGACAGCATTTCTGGAACCAGCACAGT
GTAGCCTAATGGGAAGCCCCTGTTAAAGCCCACTTAGCGCTGGGATAGGGGGTGGGTGGACCTGGAAGGTTCTGG
GAGACCTTTGTCAGGAGGTTGCTGTCTTTGTCCCCTATAGTAAGTGCAGTTGTCCGCTGGCCTGATGGTGATTGT
AGGCGCTGTTTGAACCTGTGTGTTCCTGCCTCTTTGGGCACTTGCTCTGGAGAGTCAGTGGTTCAAGGCCAG
AGCTTTCTCTGGCGTGAAAGACAGGTGCTTATAGGAGGGTGAAGAGTAAGACACTAACCCAGTGAAGTAAGGTTA
GCTGTGGCTGCTGAGATAGGCTAATGGAAGGAACCCTGCGCCCAGCACATCGGGGTGGTGGGGTTGGCTGCAGC
ATCTGCAGGCTGCTGTGGAAGGAGCGAACAGTGGAGACAGAAAGCACGGGAGCATTTTCAGCTTGGAGGCAGGCA
GGCCCTGGCAGTCTCACCACTTAGGGAACAGGCACAGAGGACGACGCCTATGCAGGGCCTTTGCAGTTGGCAGTG
TTGTCTTTAGGAAGGATCTTTCTTCCCCAGAAAGAACCAAGCAGCTCCTTTTCCAAGGGGCCCAGGCCTGTAGAG
ACCACATATGGGGTGAAAGATGTCCCATCATCCACCTGCCGGAGTCACTGAAGCCTGGC

FIG. 2

Clones and QP for each clone

SEQUENCE LISTING

```
<160> NUMBER OF SEQ ID NOS: 16

<210> SEQ ID NO 1
<211> LENGTH: 6192
<212> TYPE: DNA
<213> ORGANISM: Cricetulus griseus
<220> FEATURE:
<221> NAME/KEY: gene
<222> LOCATION: (1)..(6192)
<223> OTHER INFORMATION: Srxn1
<220> FEATURE:
<221> NAME/KEY: misc_feature
<222> LOCATION: (3900)..(3928)
<223> OTHER INFORMATION: n is a, c, g, or t
<220> FEATURE:
<221> NAME/KEY: misc_feature
<222> LOCATION: (4660)..(4672)
<223> OTHER INFORMATION: n is a, c, g, or t

<400> SEQUENCE: 1
agcttgaaaa tcagtcccaa gagtatttat ttccagcaga gtaatggcag atgctgtaag      60 ctagggggctt cccccaaaca ctaggtgcgg agtatttatc tacatccatg tgaacaatat     120
accctgtgct cacttagtac acacttggga gacacagtac acccaggagg caaggacagt     180
ctcaccctga cagggtttct gtcccaggaa cagactgaag gaggaagtga atcagggagt     240
gataaacact atgaagacag tcttacagat gacaagccag gatggaagga ggccatgggt     300
```

```
ctgtctgaag tgacaggggc acagaaccac tagggaggct acggaagcta caaatatgga    360
ctagtttagg ttaagagccc aaatgcctaa gccatggctc ctctgaagaa cagtagggac    420
cagtactggg caggtagccc ctatgttcaa cgagcagggc agtgggtgaa gtccgggagg    480
actccttgga agggtggccc tggacagctg catttggtag gccttgtgtt gaaggtgtga    540
gagggtaggt ttaagaatgc tcccactggg gctggagaga tggctcagag gttaaaagca    600
cagactgctc ttccacaagt cctgagttca attcccagca accacgtgat ggctcacaac    660
catctgtaat gagatctggc accctcttct ggcctgcaga cagaatattg tatacacaat    720
aaataaacaa gtaaataaat aaaggcccct ctggatgccc atttcctaat ctttaggacc    780
tgtgaaaccc accttacata gtggaaatct gctgatggga gtgggcttta aggctcctga    840
aactgataga ttgtcctgga ttacccaggc aggctgaatg taatcaccag gttctttgaa    900
agcaaaaggc tgtggcaaaa gaggtcacca gctgctgcta ttttgaagat aagggagagg    960
ccctcagctt aaagggttca attgttaact tgatgaaatc cagaaccact ttggagggtg   1020
ggcctttatg gatgcctgtg gggggtttata gtggttactt taactgagat gggaagaacc   1080
acccactgaa ggtggcatca ttctctaggc tgggatcctg tactgtataa agagaagaca   1140
ctgagcagtg cacaagtggt ttttcaccat tctgactggc gatacactgt gaccagtggc   1200
ctcaagcccc tgccatcatg acttccctga tgtgatggac ggtatccttg aactgtgagc   1260
caatgtaaac cttgttaccc ttaagttgca tttgtcaggg cgatttgtcc caacaaaggg   1320
aaaagtaact gagacttcag gaaatgcatt ttcccttaag gcctcaagaa acagtcctg    1380
ctggctcctt attttagctc aataaaacac actttgagct gggtctggtg gggggtacct   1440
gtaatcccag caccagagag atggaaggtt tcagactagc aaggctatat agagacacac   1500
cctgctttaa aagcagcaaa acaacaacaa caacaaacaa caacaacaaa aaaaaaaccc   1560
acaaaaaaca cagctttgga ctcctatctt gttttaagcc atgtttgtga caacgtgttt   1620
aggtggccaa agcagatagg tccttgtctc cacaagagcc tgtggctcca gcatgggaca   1680
gaggtttcta aactggtctt ttaaacccat caggatccca gctgtgctag ggggcaccca   1740
ggtggctgtg aggtcacaga aggcctagcc aatagggtg gcaggggag acattgacac    1800
caagacagaa agactaagca gttagaagca acaaagagat aaaaactcgg gcttcagggc   1860
attggtgatg ctcccgctga ccgtgccaga gctcctaagt gcaatcccta gcatcatgtg   1920
cacaccaaaa ctaaaacaat gccgagaagg aggtgtggga gcacttcctg gggtgaggta   1980
agtctatgca aaggcccagt ggtactcaga gagcggtggg gctaagtccc cttcccacag   2040
tcagcttgaa ggcaactgcc aaggtggcaa aataattgct tttgtgaaat tctcacagga   2100
agacaggggt gcaaattta agaccaaaca tcctcgggac tttagggggtt ccagggccca   2160
ctgctcaaga atctggaaga atcttgatct gacacaaacg ccctagcttc tgcggggact   2220
ctccctccaa tatggaggcc ttgagcctct cctacttccc aacatacatg acacacccag   2280
accactgccc tgactgtcat ggccagaaga gacatcagga tacccaggtt atctgggggt   2340
aaagtttcat tgtatcatct tgtaagtgct tgacctaagg caagttgctt aaaaaacaga   2400
acaaacaaa acaaaatcca agcttcctgt gcctcagttt ctcctccata caggaggaac    2460
cgcagctact tcacagagct gatcagagaa gctgaaatca gctgggagca accgcagcac   2520
ttttgagtat gtgcgtcaca gatcattact ttcatggtca agtccaagtg aggaacctga   2580
ggcccaggga ggctccgcca gcccagcccg tcaaggtcac acaggcgaag ctgagctccc   2640
gcagatcctg gacccctacc ctcgcgccct ctctttctcg cgcgggccgg taggctccgc   2700
```

```
gggctcacca ggatcgtgtc cacgaggctc tgcaccttgg ccgggtccag cacggatggc    2760
agaggccgga tgagcacgct gattggcacg ttgtgcaccg tggtgatgca gcccgagtgg    2820
atgctgcctc ccttttattt ccagcagagt aatggcagat gctgtaagct aggggctttc    2880
aacccatcta ccgactgccg gctgcggcgc cccgccaccc cctcgcgaca cacgcagtgg    2940
acgcgtccgc cgctgactca gggtgagtct gcaagtcgcg gagcaaagtc gcgagtgacg    3000
cacagagcgg tgactcaggc tctgagaggc gaggacgcgg gaggtcagac ctgcccagca    3060
agaaagggtt ggctctcagt gggagctggg aacagtggcc cccacatggg gaaaacagga    3120
atgtggtgac ctcacacttc agagccaccc tgctagctgg gcacaatgtt aatcccattt    3180
tacagaggag gaaactgagg cacagagaag ttacgtcaca cacatacaca cccaacacac    3240
ccacacacag gcttggagct aatgagtggg tgagctgagg cccaaacccc ggcaggctcg    3300
ctccacggat ctctctagat tccaccgcgg gctccctgg gctcagcgac aagaactagc    3360
caccgcgcct tctggagttg tgttgattct gtacgtcctt ccatgaaatt ccatattgca    3420
catccccaag ctatatccag gaagtaggag tgggagtggt tactgaaggg cctccccaaa    3480
gtagtccccc tgcggggtgg gggtggggag agaggaaaag aaaccaaagt caggttaccc    3540
gactgcgcag ctagagtccg gctggagctg tggcggggtg tcaacccgaa cagctgcaca    3600 cgcccttttcc tgtggcttgc actgcctcct agctggcgcg tgatgtccag cgatgagcgt    3660
ccctagaaag gctgggccta ttccaggtca gcctggacgc cgtacaggac ccactctgtg    3720
actttctatt gggaagctga tacaagcctt cccaggccca agggaagggg acagtgaaag    3780
agcctgcggt ttgggacctc tgggaccgct cttaggagag agagctgcgg atggaggtga    3840
cccggctagg tgctagagaa aggaaccgcc aaggcagact cggctaacgg ggagggctn    3900 nnnnnnnnnn nnnnnnnnnn nnnnnnnnag gactctgcat cactctaggg acagagactc    3960
tgccccctgc tctttcctgg gcaagtgtgg ctggaggtgc tgagcctagc cttacctggc    4020
taccctgctt ttgagcggag caggcatctt aggggcccag aagcacacag cggtctgcct    4080
agggtgaccc gaggtaatca aaggatcaca aagctggctg gctggagtag gaggtgtgaa    4140
ggaaagttcc cagaaaaaca aacgacgaca acaacaacaa caacaaagca aaacaaacaa    4200
acaaaaaacc atcttcaccg aacattacag gctgatggac ttacaaaact tagtgattgt    4260
ggagaggttg gaatgttgcc agtccagagc caaatatcct acactatcct taatcgtccc    4320
cgtaactgtt tattgcccgc cctcgtgtga cctaacttcc ttttaggata cactgataca    4380
caactagctg acacaaaccc acaagttcag gatgtctccc ctggcatcac aggtacagac    4440
ctgtctctga tgtcatagct cacttccccg gatgtatatg gttttaagcc attgattaat    4500
tcatgttggt gtctgcagag tccagaagag ggcatcagat cactagggac tggagttaac    4560
agaagaatgt gagcctcttg tagatgcagg aattgaacct gggtcctctg gaggagcagc    4620
cagtgctctt aactgctgag ccatctctcc agcccctccn nnnnnnnnnn nngattttt    4680 tttttttttt tttttaaga tttattatgt atacagcttt ttgcctgcat gtattccagc    4740
acaccagaag agggcactag atttcatcat agatggctgt aaaccaccaa tggttgctgg    4800
gaattgaacc caggacctct ggaagagcag ccagtgtctc taacctctga gctatctctc    4860
cagcccccca cccccacccc acccccttgga tgtatttaa gtgtgttgat ttacctactt    4920 tcttttgttct atttctgcta ataattcata aaactgttat catgttggaa cgtggacttt    4980
taggtgacct aaatactcca gagtcacactc ttacccctgg gagacgacga gagctgtgtt    5040
```

```
ttttatgttg ccataggctc ttgctccccg attccttctg cttcccccac ctcagctgat    5100
ggacttggag gtgacacaga cagagaatcc tgtttatgaa acatttggac atacaggtga    5160 cttccccaa gtgtttggaa ggtgaaagga ttatgggtcc ttccgtttga agcccctccc     5220
caacctgctt gaccattct ctagcttagg cgtcagggct ggcttccat gttgtttgtc      5280 ccacagcacc tcattctttg gtgttcactg agcatttctt tgggggtgca gaggcagctt    5340
tgcactccat cttctcacag tctcaagaga gctgccagtg tgaagccggt ctcacttttg    5400
ttcacaccca ggagagggag ggagggaggg agagactaca ccagcagtgg tgacatcaag    5460
tgctttcttt agtcagtctg attgggctag cttgagtcac ccaggatgac tggcattctc    5520
cagggatatg ccgtgtactg agccgttaaa gcatggagtc tgtcaccaag ggggacgact    5580
gtgatgaatt tagaggggac agtcaaccac ccttctggga tacagcctct tctgagtcac    5640
ctgtatgtgg gtgaaatagg tgggccgatc ctgggtgaat atgaggctag tgggtgagag    5700
atggatgctg acaagagaaa gatgcgccag aggcctgggt gtcactgcct tgtccttag    5760 cccctctga tgttagctgc aattgtgcca gaaagttcta cagcagatga ctcactcagc     5820
accaccagcc cttaacccag gtgccctgag ctcccacgtt gatctctgcc cacacacagc    5880
acatgccagt gctgtcatat ttgccgtggg agtagaacac gccagtcttc caccaacaca    5940
ggttggcaat attaatcatt tggatctttc tggactgttc tcagagatca gtggtaacca    6000
gcctgttgct ctagcagggg cttcacagac acacccctga cattcttcct gctgctcact    6060
ctgccacttg ggctcccact tagcttgcac aagggcctgg agcctctgcc tttgtcagtg    6120
ggaaactaga acctcagcta agagcaccat acattgccat accctataat ttatgcccca    6180
cctggcttaa aa                                                        6192
```

<210> SEQ ID NO 2
<211> LENGTH: 192
<212> TYPE: DNA
<213> ORGANISM: Cricetulus griseus
<220> FEATURE:
<221> NAME/KEY: gene
<222> LOCATION: (1)..(192)
<223> OTHER INFORMATION: Srxn1

<400> SEQUENCE: 2

```
cacagagcgg tgactcaggc tctgagaggc gaggacgcgg gaggtcagac ctgcccagca     60
agaaagggtt ggctctcagt gggagctggg aacagtggcc cccacatggg gaaaacagga    120
atgtggtgac ctcacacttc agagccaccc tgctagctgg gcacaatgtt aatcccattt    180
tacagaggag ga                                                        192
```

<210> SEQ ID NO 3
<211> LENGTH: 6164
<212> TYPE: DNA
<213> ORGANISM: Cricetulus griseus
<220> FEATURE:
<221> NAME/KEY: gene
<222> LOCATION: (1)..(6164)
<223> OTHER INFORMATION: Adh5

<400> SEQUENCE: 3

```
acctctaaga ctgtggaacc ccattctgat ctctattaca gtggctggga gacaagctaa     60
ctgggtaact ggaaaaactt ggggggctaag actatgattt aatggttata atgaaggagt    120
cttatttacc atacaacaat tcatagtccc tttacatggg cccatcccag ttggctcaaa    180
tccagttatg aactccttgg ttcaactcac aggaccaccc cttcccagga caatcatccc    240
```

```
ccttaataat gtcagtccca ctagaaaact ctcccagccc caaggaccaa taaatcatgc      300 tttctctcc tactggctat agatgtttac tataaataat tataaataat tctcagtcaa       360
actggaccag acctgttggt tatgtttaga cccctctcct ccctactatg agggcataac      420
agtcatttct tcatacaaag aaaattcttc ccgcataacc tgcccatagg gaacccaccc      480
caagcttaca ttaggatcag cccactggcc tttgtatcct gccatctaac aaacccattc     540
tggaggctta tctgcccctc tgagattcca cctacttatt acagcacttg caccgcctgt      600
tacctcacag cacctgaagg cacctagtgg gcatgctcca tgtgtacaca cccagatact     660
acaacaaaac tcagaattct gtgtcttcat tcagattttc ccccaagtcc tttattattt      720
tgatgagacc atgacaaccc acctagccac cttccctcca cttgacaaag gtagtctccg     780
gcactccacg ttccaacttt ggcaggtctg ggaatagttg gggttacccg aataggcact     840
actgcccttg tgttacaata tgaaaattac aagacgttag gtgccttgag tgatcaagat     900
ccggccaagt tagaaaaaaa tctatttccc acctagaatc atcccttagt tctttagcat     960
cctcagtgct acagcaccac ccaggattag acctcctctt ccaacaggga aaacatgcct    1020
ggagctggga gcacaatatc gcttctaatc actcaggggt gataaaagaa tctgtgcctg    1080
gtatgtaaaa ggttacaata tcgagaaaaa caatggagga acagttctga ttggcacgaa    1140
cccttgttct catggtcatc atgggccacg accttaataa ccgcactggt aggaccccta    1200
ttgatcctgt tgctagttct gatttggagc gatgtatagt caacactctc ctccttatta    1260
taaaagaatt cactggagca attaaatgaa tggtcctttg cagccaatat aggcctctgc    1320
ctacaaatga cacagaactc acattaagtt caaacatttg acttttgttt taactcaagg    1380
ggggaatgaa ggaactaggg ccagttgttt tttaagggc cagtttgcta agacctctgc    1440
cccatattac cccataatcc tatgactcat gtcggacttc aatcagaccc tcaggaagta    1500
tgccgggccc ggtggccaat cgggtcctac ctgaccacac gtaggaactg ttcttgctat    1560
cttcaaacag aatcttggca cagcagactg aaccctgaca cagccaccac agctgctgac    1620
cagatgtcat tggccaatca ctaaagtctc tcctgaccag tcagggtctc cacccaaatc    1680
acttcatgcc taaccacagc tggaattgcc ctaagcaagc ttaaaaggga ccacctcact    1740
cctccctgta gttggtgcca ctttgggtgg accccagcat gcgaattttt ctgtcttgag    1800
aacaaagctg ctttctgcaa ttgcatgtct gtggtcttct ggtcattagg ggcgacctaa    1860
gggccctaca ctgtgattct cgggtttctg gctggagcaa gtagatggac acacctgcca    1920
tcaacacgga gatgtaaaga aaggtccctt taagaagaaa atacaagact ggttttaagt    1980
gagttgagtt ttaagcacta tgagctaccc taacacacac gggtatctag caggcacttt    2040
gcacttcaag cctggagttt aggaaagcca ccctgactgg agacagaatc cggtagtcac    2100
cctataatca ttttataagt taaaagtcgg agtgtgagtt agtgtgaaaa gagggaagga    2160
cttcaaagag ttttgtggaa aacgtcaacc cttaaggtct tgtgttgaag aaataagcct    2220
tggaaaatac aaagagaatg cggtgtcttt gcaggcacat ttcaacaaaa cctccgtgtg    2280
tcctggcagc gtttaggatt acgtaagaac gcagcatcct ccggctatac acagacgctc    2340
tactctgaaa acgcacccat tctgtccctc gttccgtgtc ctatggcccc gggaagctgc    2400
tggacccgga gccagggcag gtgcttctag gacggcccct ctcgcccag agtccgcgt    2460 taccacgact cgccgctggg ggcagtgttg acgcatcccg tacccggaag cgccaagcgg    2520
ggggaggggg aggcacggaa ggcggggcta gttcctcacg tgcttcaggg gcactgggtt    2580
```

-continued

```
tcctcgcgtt gttcctctct cacgtctaag ccttacgtgc gagggctcac caaagttagg    2640
cagggaaata ccacagagac gctttgcagc gactccgtca gaccagcccc gaataaaaag    2700
cgtcaccgac tctggataaa atccccgccc tcgccagcag gggagcgcgg gagccaaaac    2760
ccaggctccg cccttccggc gttagcccct cctccctctc aagctccgtc cctctgcacg    2820
cggcctgagc atcaaggtcc cgcctcccgc gctcggcccc gccctcgcg cacggcccgc     2880 ccattcccgg gatccgctag gcttgttgcg gacgttttgc tcgcgaacca cagcttgcgg    2940
acatggcgaa ccaggtattg aaacgcggca tgggcccgag cggaggaagg gagcgcccgt    3000
ggggtatgcc gccgcagcg ggggaggcga cggcagggag gctttgtttc ggccctgcgc     3060
ttgggagcag cccgcgggaa gaggcgggat ggagtagctt gcccggatcg cacttgcagg    3120
atggcgatgg cgtagctgag cactggccgc gctcaaaact gccaagcaaa gtcaggctct    3180
tccttgggcc ttcgctttcc gtgtgcacca ccgtgtacat gtttctttaa atcacgtctt    3240
aagtgtttat tgactttcaa gcccatctcc tgtaaacccg gtggcttgca acctttattc    3300
tgtcgacata tttcgtaagc atcaagtgaa ctaacaaaac ccaacattcc tcattaggtt    3360
cgcttctggg gtaaggaaga gctagctcat tgctttagat gcacgataaa aaaactgtat    3420
atggagtttt aaacttttcca agaaccacat ttgagaaaga atagataaaa gtaattctaa    3480
tgctatgttt acccaactta atagtcacag tattgtttca aattgttagc tgggatattt    3540
ttactcttct aagcttttcaa aatttacatc catagccaat ctcgggtcac cctgactttt    3600
ttctactgtt cagtagccac acatggcaaa tggttaatgc attagctagc acagttactg    3660
tggggaaaag gggccagcca agaaacgca ccctgagcag aaccacagaa acacactttg      3720
gccctagaat cagccaaatt tgactcgaaa cctggcagaa aaccatccaa tccctgagca    3780
caagatctag ccagtctgag cttagtgatt gaaatctgac caatccccac cctataaatc    3840
tccctgggaa aactccaccc ctaagaatcc ttatataaac cctgtacctg ttcagcttct    3900
gactgcttga gctgccagct gtcctctgcc accctggaat tagagccagg tgaggttgg     3960 gtgagacctt ccttcaccac tggaatggag caagcaaggg gagcagggct gtaacacttt    4020
tgctggggaa accttcccct agcaaagtga agttgttaaa ctctggggac cagagcctaa    4080
ctataacaat ttcacctggg aagccctccc ctgctggagc agagctgtta cactagggaa    4140
gtcttccccc tggagcaggg ctgtaagcta ctacacttgt tgtgacttgt ggtattcctt    4200
ggctcccgat tgccagaata cttttccacc cgagctgtaa cactcagtat cctgtggctc    4260
ccgagtgcca aaattccatc caatccacca caatgcttaa agctacgaga gatggttatg    4320
gtatttttac atatccccca tttggatttt tttaggatcc tttccactat gtagttttgc    4380
actacagtgg tgttttgtaa gctttaccaa gggaccccag gaaactagtg gctttcagca    4440
gagagcaggt acatagggac ccttcaatta cttaccaaac ctactgacag gacctgggtg    4500
ggattttgtt gtttctctta cctggcttgt cttttgctgt gttggggatc gaatccaggg    4560
ccttgtgcat tagaggcaag tgctctgcca ctaagctaag caacatccct agcttttgg     4620 acaatgtctc actatatgac tcttgctggt ccagaacttt atgtgggcct caaacagaga    4680
tcctcctgcc tctgcctccc aagtgctgag attaaaaatg tgtacctcca cacccagcag    4740
gacctgtatc taatctgttc ttttccatac attgtacagt gtcatgagca tttcaattag    4800
atcttttttt taaaatagtg tttactgtgt gtgtgtgtgt gtgtgtgtgt gtgtgtgtgt    4860
gtgtgtgtgt gtgtaccacg tgcatgcaga agcttgtgga agatacaaga aggcatgggt    4920
cctctggaac tggagttaca agtagtcttg ggcatgtaga tactgagcac tgaactgaga    4980
```

```
tactgagtcc tctgcagagt gacatctctt cagcctttcg aatagtgtgt gggggcgggg    5040
gttgtagtag tggtttctcc agggagggtt tgagataggc tctctctatg tagccctgtc    5100
ctgcaacttg aaatgtagac caggctggcc tcaaactcac agagatccac ctgcctctca    5160
agtactggaa ctgaaggttt gcgtcactat ccctgaccct ccaaatatat gttttttagta   5220 tatgaattat atgaaaccta aaaaacagtt ctccattttca cacagaggta tacgtttttc   5280
tgtgaatgtg ctgttcactt tagttgtgtg tgtctgagtt tgtaatgtgt gtgagagtgt    5340
gtttgtgtat ggtcacgtgg aggtctgagg ctgacatcag gtgtcttctt caatcactct    5400
gcaccatctg tattgaatca gggtctttca cttgaaccca gagctcaaca gtacagttag    5460
tctagccagc cagcttgctc tgaggacccc cgtctgcagt ctgagtctgc catctgtaat    5520
tacagacagg ccgctacatc aggtgtgctg tggagttgcg ctctggtcct catgctggca    5580
cagcagggcc tctacccact gagccgtctc cccagccctg gtacacgctg acattagcat    5640
catcgttatc tgaactgacc atgaaatagt tattaattta ggaggataaa ctgttcactt    5700
ccttcccccc actctaggtg atcagatgca aggctgcagt cgcctgggag gccggaaagc    5760
ctctctccat agaggaagta gaagtggccc ctccaaaggc tcatgaagtt cgaattaagg    5820
taatgtcaca gcaaggcact gtgggaagaa gcttacagtt aggtcttcgg agagaagagt    5880
ggacctgagg gccacagagg attaacccaa agggttgagt cgaggagaaa gcactggaag    5940
ccttccaact gcagagtcac agagccctct cacctgcccc ccccccttca ttctgtattg    6000
ctctggggct gagaagaagc caagcccccg gattagtgta ctatcacgac ataactttt     6060 atggtttggg tttacggtgg ctttatatga tcctctccct tctgctgatc ccataactca    6120
cagtgtggtg gattagagtc agtaagaata gacacaagct tcag                    6164

<210> SEQ ID NO 4
<211> LENGTH: 163
<212> TYPE: DNA
<213> ORGANISM: Cricetulus griseus
<220> FEATURE:
<221> NAME/KEY: gene
<222> LOCATION: (1)..(163)
<223> OTHER INFORMATION: Adh5

<400> SEQUENCE: 4
ggggtatgcc gccgccagcg ggggaggcga cggcagggag gctttgtttc ggccctgcgc    60
ttgggagcag cccgcgggaa gaggcgggat ggagtagctt gcccggatcg cacttgcagg   120
atggcgatgg cgtagctgag cactggccgc gctcaaaact gcc                    163

<210> SEQ ID NO 5
<211> LENGTH: 6429
<212> TYPE: DNA
<213> ORGANISM: Cricetulus griseus
<220> FEATURE:
<221> NAME/KEY: gene
<222> LOCATION: (1)..(6429)
<223> OTHER INFORMATION: ASPDH/JOSD2

<400> SEQUENCE: 5
gagtgacaca gcatgaggcc ccagaggccc ttggatactg cttccctccc cagaacagcc    60
actcaccacc cactgacctg tcaccctcta cctgtcaagt ccagctttgg ttttgtttag   120
gcagggtctc aggtgtccca gatatgcacc actacagcag ttcatggggt gctggggatg   180
gaaccccagc ctcatataca tgctgggtaa gcgttctgcc aatggagccc cagcccctca   240
```

```
acgttttgtt atttgccttt ttgagtcagg gtctctatat gcaacccagg ccagcttcca    300
attcagtttt gcctcaggtc aacaggctgg tctcactact cttaacccca tttcctcagt    360
catgagtcac tcatgtcact tggaccccccc acagaatacc tttcactggt accaagttta   420
tcagtttagc tcatcagtca gtcagtcagt cagtcagtca gtcagtcagt cagtccccat    480
tagccagagg ctctctggca aaacctcccc ccatctacct tcaagtcacc ctctgcttca    540
tcccacaaac ccagggccag tgtagcccac agcctaggcc ctacctcctc ctgtcccacc    600
acacagcggc caggcccagg ccttgcaggg cagccatgat cacgttgaca tcataattgc    660
cggtgcccag gaggctgcga tgagggttca gccgggagtc tggggccagc ctggggtga    720 aggggggcaga gccaaggttg ggaatcctgg aaaggccttc aacttctcac acagcaggag   780
aggcccagag cctggctttt ggctctttct ctttaagccc cacacagctc attgggctct    840
aagccctgtt tttcctccca ttcccaacac ctgtactctc tgcctagcta aagttttttgt   900 cttttttccac tcagaaaccc ttcccagtct ctagtctctc catccgatcc acctccaaaa   960
gccttgagct gcctgcctct ctcctactcc cacctctccc atgactccca agtgctctgg   1020
acaaagtctc tgcccttcca tctgcccttc tcatcatggc ctctttccag accagcctca   1080
gatgtcattt cttctggtag agaagccatc aaaccccag aatgggcaca gagctcccct    1140
gagtgacaat gccgctcatg tcaccatatt tgaatacaga atgcctcttt catttggcaa    1200
taccctgccc tactctgttc acagccctcc ctggtgcccc aaatcccggg gacagactct   1260
cacctcctcc agtggcaagt ggttcttgca tagcctcagc accagctctt accagccacc    1320
tatctccagc tgtccctgtg cccaagcctt ccctctaagc tctctccaga tgtgaccctg    1380
ttcctctgaa gagctggccc cttggagagc agtgacatgg agggaaccac ttgtgtttgc    1440
tctgtgtccc gagccttctc ctcactacat ctgccttagc tctagttgtt cagcatgctc    1500
ctggcatgac agagctggtg gcaggggat ggatatctcc taacataaat ctacagtctg    1560
agggtgctgg ctgagcagca gtgagaagat gtgaaggctg cctctggatg tggacatgaa   1620
ctgcaggctg gggtgttggc gtatctgtga aaggattgtg gggcctagaa gtgggactag   1680
gaagagagtt taagaaagtg atggttgaaa ttctgaaggg cacctacgtg accaagaaga   1740
acaagaatgc ctgggtaaga gctcagaatc accacagtgg ggtcatctgg ggccaaggag   1800
agtagtgaag gagaagctgc agactggtag gcaaggacca gagcacccaa agccttggag   1860
ttcaggctga aggacctggg ctattctcta ggagtgccag ggacccccag aggaataaat    1920
gcagaggagg gggaaggcag ctgtggggct gtgtgtagga tggtcaggag gagaaacaca   1980
gacagctggg aggctgtgac aaaggctcag ataagagagg ttgaggccaa agctgggttg    2040
aggctgtgag aagcagcagg tggaagggca gacatcagct ccaggatctg cgccccggcc   2100 tgttagtgc ccaggcaggc tcccatgccc ctcagccctg ctcttccagg gccaggacct    2160
agggcagtca cctcttgcaa atttcatctg cagcttcctg gctaaagagc tgttgttgga    2220
ggacgttgtt gagagcgtgg accgcgcaca gctctagccg ctgccgctcg tggtacactg   2280
agggtgggct cggccgcgct tccggggcct gagacatgcc ctcctcggct cctgctgggg   2340
gtggtacaag gagaaagtgt tagggaccca ggatctcggc catctgggtc tccagactcc    2400
tgtgtccctg ggcaacagcc actgagatgg gcactggagc cagcttggga ggaaacgacc   2460
cagctaccta ggctgtctcc gaagcgtaga ggcatcttta tgcccagtc ctagggggaa    2520 agggctcttt tttgctcact tggcaataga gatccacccc cacttcatgt ctctaagcaa    2580
aaaaaagtcc ggatcactat aacctagtaa cgaagtatcg ccccttctgt ccctaggaaa   2640
```

```
caataccttt ttggttccca agcaacagag tactccccac ccgcttggta accggtccga    2700
tttctgatca cctagcaatg gaggactcct ccttccccgt ctctgggtaa cagggtctct    2760
tctggtcgcc tagcaacgaa agacttcccc tcatcaataa ccagggttct ctcctcccgt    2820
cacctggcaa caaggccctc tcccagtcac taagcaacag gagctcccct cttcctgtca    2880
cctggcaacc aggcacgctc ccacccgcct ccgcacggca ctcgcttggc cctcaccccg    2940
tcggcctctc tgctcgctgg gaccggccgc tttctcattc cctgggtagc ggccgagtgg    3000
taccacgctg actgggcagg caggacggac tacagctccc gaccgcccga gcactcctga    3060
ctgcaattcc cgaaggcctc cgaggcgcct aaataggacg cgcggtacgg aagtccgccg    3120
gggacgctct gcagcgcgga actacaactc ccgtcggacc acacagccag ttttcatgca    3180
cccccagggc tcactgcagt ctagaggttt ctgggaaatg tagtaactgg ggctctcgcg    3240
atagcttcca ggaaaatggt ttgtgcgtat gctcgtgcgc tcgctgctat ggcgtcacac    3300
acagtgtgtt gaagcgtgat gtaatagagt taggggataa ggaactaaag aggccaaaga    3360
gaacagccga cagaactctg atgtttactg agacacacag tggtcgaggt gacagcaagg    3420
gcagcggggg agacttgtca gcagaggtga atcccaggtc tggaggggag ctggcagcag    3480
cctgtgggga gaatgaaaga ctagaatgac cacacagaca tgcaagcagc catggcggcc    3540
gtgggctttg aaaatgatag tgtagtacaa cccaaagagg atactcagaa agagatgtgg    3600
ggtgtggatg cagagacaag agggggggctg agactcagag aaaaagagag acctgggaga    3660
gaaaactaag gatgggcaaa gacagacaac cggggtggga catccgacat gtgagttctg    3720
cagggcacaa aagtcaaggg actcttggag aggtctggac gcacccagta ggctgcccca    3780
gaaggctgtg acagtagcag agccggtgac agcgccaggc tgggctgggt tctctctgtg    3840
ggtgtgcaca gcaaagctgt ggcctgtggg ccctgggggg cctttcagct ccacgtccac    3900
cacgtgcatg tcttgaggc tgcagccagc ggagaagggt agttagtaca tctggcctgt    3960
acacaggtgg gccacttact tccgttgctc acctaaggtc agccacaagc accccaatga    4020
cacggtcgaa gcctagactg ggggcagcca gggcagcagc tgccatggtg ttagaatttc    4080 gggggggccaa ggggcagagc ccacgcacag ggccctcgta gagcactgtg cgcggcccac    4140
tgatgtgtgc tgcagccagg gacccctcca gtcggaagcc atcaggatgt gtggccatgg    4200
tgactcgaag gctctggaaa caatggcagg gtcaggaagc tgagactctt acatgttccc    4260
tcagttgcag cccatatggt tctcacctgg aggcctcccg atgcatccaa tctcctgatg    4320
tcttcagtcc cccacagggc tcctcgggcc acaaacacag tgtggcccca gcagtttgat    4380
gcctccatga gctgctgctc tgtggtctgg tcagccagag ctgagggaga ccccaccttg    4440
ggaagtatgt agagagagg gaaggccaag acatagatca ttgctgtgtg gtgggatgca    4500
gccaacacag agaagggctt gctgagggat tagggggctc accaggaggt tagcatgtcg    4560
caggatttgt acccctgatt catgattat atttggatgg gccacttcta ccacaaggtc    4620
aggatgcctg ggagagggag acatggagta ggcccttaga gaagaatcag gtctcagggt    4680
ttggagggat gtcactcctt accctggcta gggagggaaa tgggatggtg ggtgtattct    4740
agtttatctt tatgtgcact gagacccaga gagggtcaaa gtgttgtctg acactgggag    4800
gcaggcagta aggctcccac tgtgctgtgg gccactgacc tttccttaag ggtagtaagg    4860
tcttggagct gcagggcagg gggcacactc cctgccattc gtccagggtc acggttccat    4920
acaaaaacaa gttctaggcc cagttctggt ccctgagcca gaaggcgaga cacaagagac    4980
```

```
tgtcctgcag aagggggagag ccagagatcc aaggaaagta cagagactac accccagtca    5040
tggagatgga gaggggggaca gagagagata cacagacaca gaggaggggg agggccagtg    5100
acccaaggaa agtacagaga acacatccca gtcagagaga cagaggagag agggacacac    5160
acacacacac acacacacac acacacacac acagagagag agagagagag agagagagag    5220
agagagagag agagagagag aaagactata tagacaccaa aaggggagag acagagactc    5280
agagacacac agaaagaggg acaaagacct agaaagagaa aaagagagag agatgagacc    5340
aagaggaaag atagaagact gagataccctc agagacccag agagagaaca gagacctaga    5400
gagaggcaga cacccagata cacacacaca cacacacaca cacacacaca cacacacaca    5460
cacacagagt gggggggcac gacagagagg accagagaga ggaaggccca gcaagtgggc    5520
agaaggcaga ctgagctggc agactgggga gaaagacaag tgggagcaga tatttctggg    5580
acattaggga tagggccaca ggaggaggcc ctaggctagt ttggactcac ccaggcggcc    5640
atagcctacc accccacct tctggggac ttgagggact acactggtgg ccatggcctt    5700
tagcacggtg tcctgttgta gatcttcagt gtttgttggt ctctgtacca gacctgggca    5760
gtgaatgatc tttgtagttt aacccttgac cctctccact ggagccagag ggaggagca    5820 gggtggtagg gatgaggtgc ttctctgtga gccctctgcc ctcctgtgct ggctggcatg    5880
gtggcttgcg agctaggcct ttgtggccct gtgtgctcac taccccactg cctcctgtgc    5940
agccacattc tcccatccct catgaggtgc agtccccct cctcaggctg aacagcaggt    6000
tgtcatggaa attgcatttt gcttgggata ggggaagaac tggggactag aacttgggtc    6060
ttccactagg tcccttacag acctcttgat ctctgttatg tggaaaggtc tggctggagt    6120
gtcatgtggt tcggcatgcc acactgtgtc ctgtctttct cagtcctcca tgcccctcag    6180
tcccggccag agtccctcc cccaccccag tgtctaattg cccttgaggt cacagtctcc    6240
tgcctctttg tattcctggt cccctgcctc ctctcccacc tcctatccca gccacgaaga    6300
agggggtctg catagctggg ggagttccta agtgtcccca ggatgagtcc agccactgcc    6360
tgtcaggcct ggcatgggac atggcaggct gcagtaggcc agctccctgc ccccattgcc    6420
acctggtac                                                             6429

<210> SEQ ID NO 6
<211> LENGTH: 255
<212> TYPE: DNA
<213> ORGANISM: Cricetulus griseus
<220> FEATURE:
<221> NAME/KEY: gene
<222> LOCATION: (1)..(255)
<223> OTHER INFORMATION: ASPDH/JOSD2

<400> SEQUENCE: 6
taccacgctg actgggcagg caggacggac tacagctccc gaccgcccga gcactcctga     60
ctgcaattcc cgaaggcctc cgaggcgcct aaataggacg cgcggtacgg aagtccgccg    120
gggacgctct gcagcgcgga actacaactc ccgtcggacc acacagccag ttttcatgca    180
cccccagggc tcactgcagt ctagaggttt ctgggaaatg tagtaactgg ggctctcgcg    240
atagcttcca ggaaa                                                     255

<210> SEQ ID NO 7
<211> LENGTH: 6538
<212> TYPE: DNA
<213> ORGANISM: Cricetulus griseus
<220> FEATURE:
<221> NAME/KEY: gene
```

<222> LOCATION: (1)..(6538)
<223> OTHER INFORMATION: Tenm3

<400> SEQUENCE: 7

| | | | | | |
|---|---|---|---|---|---|
| cagttacctt | gtgtacatca | cttacaacga | gcaattcgaa | gagaaagcta | aaataatttc | 60 |
| ctggacaaca | ccatgaaaca | ggctaaaata | cttaggaata | aaccaagtta | taaatgtgaa | 120 |
| tgttttatat | agtgggagtc | agaacacaat | gctgaatgac | attaaagcaa | accctaataa | 180 |
| atgcatctt | gggttaacaa | agtgacgttc | agacacaaag | caatccccat | aaaaccttag | 240 |
| caatgtctgc | tacagctgca | tgcgtttgaa | acatccaaaa | acgcttacaa | aatacacaaa | 300 |
| gctggaggac | ttaggtaggc | ttatgtgaaa | atatattagt | aacctctaat | aactagtatg | 360 |
| gtactggcat | agagaaaaat | aaatcaaagc | aaacggttac | gtaacaaaga | gtattattaa | 420 |
| atgttcacat | atatgatctt | gacaaggtac | caaagctaca | ccgtgtgggg | gtgaggggga | 480 |
| cagtctcttg | ggcgaatgac | gatgggagaa | ctggatgacc | aggcacgttt | ggggcttact | 540 |
| gttcattaca | tacaaaaatc | aactcagaag | gaattaagga | gatatacaga | gccctaacat | 600 |
| tctaaaattc | ctataagaaa | acatgaaaca | ttcctgacat | tatatttgac | gatgacttcc | 660 |
| tggatgtgac | accaaaagca | ctgtcaacag | acactaaata | gggaaatgag | tgaatcttgc | 720 |
| tagtttgcaa | agcttctgct | taggtgggct | tgggagtgtg | tgggaggcgg | gcatagtgct | 780 |
| cacctttgaa | ttgcctaagg | gctaaatccc | gcggccaaag | ctccgccctt | tttctccgag | 840 |
| ggtgggggcc | agtgacctca | cgagagctcg | tcctcaagta | gaaagcaaag | aggacaactt | 900 |
| cccgccggct | ttggtggcgc | aggccggtag | gatttgctga | aggaggcaga | ggcaggagga | 960 |
| tctggagttc | gaggccagcc | tggactacac | attttttttt | cttccaagta | aatatccaca | 1020 |
| actacacggt | tcatgagatt | actcgcagga | tttaggattt | taaagaataa | tagtaaacag | 1080 |
| aagcaaggaa | gtgatcgggt | tgaggaggt | cacacctctt | taatgcactt | aaagaggaca | 1140 |
| ggaatacagt | cccagctgaa | gtccaagaga | agacagacaa | agggaagggc | gcacttaata | 1200 |
| cagaggaata | aatactgaag | ggagctcggg | ctgaaatgga | gctagaactg | aaaaattcaa | 1260 |
| tatcccatct | gttagggtca | cccgaggaca | ggacaccaga | caccttcagg | caaacagctt | 1320 |
| ttatatgtga | gaggagtcat | ggagagaacc | agaccagagc | ctagccagac | agagacctgt | 1380 |
| tccgtaccat | agtctaacgg | ctgctttaaa | cacagtgtgg | gcttaaatgt | ctttcatgtc | 1440 |
| aggaagggag | gacggcttgg | gagcattgcc | aggccacaca | taaacactttg | gtggagacta | 1500 |
| aacaggatgg | tggtctcttt | gtccttcttt | caaggcctcc | tggaagattt | actaaggaaa | 1560 |
| ggggattact | ggggagatgt | atcaaggttt | ttatacacgc | aagggcattg | ctcggccctg | 1620 |
| tggctgcatc | tggttttcat | tgccctggct | ctcaagggag | tctccctcac | atagggtcaa | 1680 |
| gcaggagata | ggatgtcagg | accgggagac | acagcagaga | aactggagaa | caatatcttt | 1740 |
| aaatcaaaga | agaaaaaaat | atttaaaagg | aatatgcaag | aatttgggga | caccatgagg | 1800 |
| cccaaactta | tgagttaccc | gagaagactc | tcaggtggaa | gaaaatgaat | ggggtatcca | 1860 |
| gagaagaccc | atggttgcaa | tgcttgtctt | agttgtgaac | cacactccag | cagtccacaa | 1920 |
| tctcttgacc | aactctcaaa | tgccatcatc | tgttgaatat | tcccaggaat | tggtccatga | 1980 |
| gttccctgaa | atccctcaag | atctgataat | gctcaccaga | cccgtcctca | cagacactca | 2040 |
| cgagatatgc | tccactaatt | tcccaggtat | ttcctaatct | tagcacgttg | acaatcaagg | 2100 |
| ctgagcatcc | caacagcata | aagttgacca | aggagcacgg | gaaagttgc | acagcatcgc | 2160 |
| tactcatcct | gaggattaaa | gtgaaaacac | cacgaggaaa | gattcctggt | ttgtcgcttt | 2220 |

```
gcttgaacga gcctggaagt ttgcagctca tcctcacaca gacaccctgg tgaaccaact    2280
agaaacctag cagttctcct aggctgtgca agaaaggtga gcacacacag gaggaaatac    2340
ataaagagac tggagttcag cgttgaagtc agtaggtcac aggcaccctg ggtccttgtc    2400
acacttgcct gaccctgacc ccgccggcac aagagggtct ggttctgcgg ttcctttact    2460
cgcagcaatt gagtctggtt cccaagaaga cgccccacgc aggacgagga gagcgagcgg    2520
gttggaagga atccacggcc ggaggtgcgg gagtgtttcc cggggtgacc agcaggggc     2580
gcggggcggg aaaggccttc ggggctcctg aagttggggt tcccgggaat gaggggagtg    2640
tgtgagccgg gcgggctgag agcaggttag agccaggccg agagcggttg gggagaaggc    2700
gaactgggcg tggtagtttt cactctacac tccgcccaca gtgttgggag ggcgagtacg    2760
tcatcgtaac tcagcgctaa ctaacggttt gatgtgagct gcttccgccg gctctggtgg    2820
cgcaggccgg aaggatttgc tgaaggaggc agaggcaggg ggatctggag ttcgaggcca    2880
gccaggacta cacattttt tttcttgtcc tccaacaaaa catccacagc tacaggctac     2940
agtaaaattc ctacacccac aaaggctctc cacactctac tctcaacctc atttcgctcg    3000
cgactgacac ccaaccgaca ccatctttc tagacgcaca ggcgcctgct ccaccctgct     3060
gctcacaagc ctttgctcac acaccgactc acacgctcca cctccgcgct ggccaatgct    3120
cgcatagtct aacggctact tgaaacccat agtgtggact taaatgtctt ttacgtcagg    3180
aagggtggac ggcttgggag cattgccagg ccacacataa cactttggtg gagactaaac    3240
aggatggtgg tctctttgtc cttctttcaa ggcctcctgg aagacttact aagcaaagcg    3300
gggattgctg gggagatgta tcaaggtttc tatacacgca agggcattgc tcggccctgt    3360
ggctgcatct ggttttcatt gccctggctc tcaagggagt ctccctctca ttgagaagac    3420
tcagtggaaa gccttcctag ttgacatagg gtcaagtaaa gacagaatgt caggacctgc    3480
agacacagca gagcaactgg gaaacaatac cttaaaaaca aacaaagaaa aatatttaaa    3540
aggaatatgc aagaatttgg ggacactcat gaggcccaaa tttatgagtt acctgagaag    3600
actgtggggt ggaagaaaat gaatgcggta tccagagaag acccatggtt gcaaagcttg    3660
accagctctc aaatgccatc atctgttgaa tattcccagg aattggtcca tgcgttccct    3720
gaaaaccctc aagatctgat aatgctcacc agaccgtcc tcacagacac tcacgagata    3780
tgctccacta atttcccagg tatttcctaa tcttagcacg ttgacaatca aggctgagca    3840
tcccaacagc acaaagttga ccaaggagca cgggaaaagt tgcacagcat cgctactcat    3900
catgaggatt aaagtgaaaa caccacgagg aaagactcct ggtttctagt tttgcatgaa    3960
ggagcctgga agtttgcagc tcatcctcac acagacaccc tggtgaacct actagaaacc    4020
tgacagttct cataggctgt gcaagaaagg tgagcacaca caggaggaaa tacatagaga    4080
gactggagtt cagcgttgaa ttgtcctcca acaaaacatc cacagctaca cactacacta    4140
aaattcctac acccacaaag gctctccgca ctctacttc aacctcgttt cgctcgcgac    4200
cgacacccaa ccgacaccat cttcttcaga cataatgact gtcagtgtac aaattaaatg    4260
aattatttac taggagctga agaccattg caactgctcg ccaattcgac tatttgagct     4320
gaagccgag ttgtctgctc cacatatttc tttccatcaa taatataggc ggctctccca     4380
ttggaggagc catcagtaaa aactaacata gcatttttta caggattgct tttaacaatt    4440
tttggaaata taaaggatg cattagtgta aattgcaaca gtccatgagc tggaaactga     4500
atatcaattc tccctaaaaa ctgatcaaaa gcaatcgccc atgaatcact gttttggaac    4560
aacccattaa cctgatgctt ggtgtaaggg acatgtatta tatttggctc tttgccaaaa    4620
```

-continued

```
tacttcctag cttttacaag gcattttgt accatgcagg ctactgcttc aaaataaggg      4680
tctaatactt tggatggcga gactggtagg tgtagccaga gtaatggtcc ctcctgccac      4740
agaacagaag tcggactatg ccttgtgggg agtatataag cctcccatgg ctttgcatag      4800
tcaatataac atatttgttg acgctgaatc gcctcctcca attgtagcag gactcgtcta      4860
ccttcctctg ttagctttct aggtgaattt ggatcattat ctcccttttaa aatatcacag     4920 agcggtttca aatcaccagt aggctctctt taaaaaggac gtaaccattg aatattccct      4980
attaattttt gaaagtcatt taaggaccgt aagctatctt ttttaatctc taatttctga      5040
ggtctaatct ctttagcata taacatatga cccaaatatt gaaaaggtgg ctgtctctgt      5100
accttctctg gagcactcac taagcctgct ctcttgagac tttgctgtag ctgtccataa      5160
atctcgagca gaaccgcttc atatttatgg acaagtaaaa tatcatctat ataatgaaca      5220
ataaagactt gtggaaatct gtccctaacc atttgtatag ctcgagacac aaacttttgg      5280
cataaagttg cactattggc catgccctgg ggtaaaacct tccaatggta cctcctcatg      5340
gctctttaaa attaactgaa ggaatgctaa atgcaaacct atgacagtcc tgaggaacca      5400
ggggaatagt ataaaaacaa tcttttaggt ctacaacaat cttataagta ccctttggta      5460
cagctgcagg aatgggtaat cctggctgta gtgctcccat tggctgcatg gttttattaa      5520
ctttcctcaa atcttgtatc agcctccatt tccctgattt cttctaatc acaaaaatag      5580 gagaattgca tggggaattc gaaggctcaa tatgaccact gtccagctgt tcctgcacca      5640
accgctgagc agcctgtagt ttctcttctg ttagaggcca ttgatctatc catattgact      5700
catcactttt ccatacgatg ggatctgcat ggcgtgcagg cttctcagtg acctcagcta      5760
aaagtgtcct aaccctgcat tgggatgtct cctgctggct gaggcgggaa caacattcct      5820
ctcactgccc tggtcccctc cttgatgggg cgacaaccct tgctgagata cccgattagc      5880
aacaattgca cttgggctat acaagtatat tcccatccgg gccataacat ctcagcccca      5940
caaattcaca ggcaaatgag gaagaatgaa tggctgaaaa gtcccttat gacctttagc       6000 atctctccaa taaagctcat cgctactctg ttcaggattc ttcgtctgac caattccttg      6060
taactgagta atagtctcca ttttcggcca cgtggaaggc cattgactgg ctgtaataac      6120
tgacctatcc gggcctgtgt ctaaaaggcc ggaaaaagcc cttccattta catataatct      6180
ctgggcgttg aggaccgata gcctgcaacc aataggcatc agaagaacca aacccagaat      6240
ctcctctctt aattctctta acctgattgt ttgtcctcac ctggggaagc aaaatcaact      6300
gagcaagcct ctgtcctgaa ctcatcaccg aaactccatc aggagaatga atcacaaccc      6360
ttgtctctcc ttcaaaatca gcatcaatca ctcctggaaa caaaaattcc ctgcatcgtt      6420
gtgctactcc tccctagcaa caatccaaca gttccactcg gcaaaggtcc ataaacacca      6480
gtgggtaacg ctgatatctc catctctggc gttaaaactg cgtctgtggc tgaacaga       6538
```

<210> SEQ ID NO 8
<211> LENGTH: 538
<212> TYPE: DNA
<213> ORGANISM: Cricetulus griseus
<220> FEATURE:
<221> NAME/KEY: gene
<222> LOCATION: (1)..(538)
<223> OTHER INFORMATION: Tenm3

<400> SEQUENCE: 8

```
cgactgacac ccaaccgaca ccatctttc tagacgcaca ggcgcctgct ccaccctgct        60
```

| | |
|---|---|
| gctcacaagc ctttgctcac acaccgactc acacgctcca cctccgcgct ggccaatgct | 120 |
| cgcatagtct aacggctact tgaaacccat agtgtggact taaatgtctt ttacgtcagg | 180 |
| aagggtggac ggcttgggag cattgccagg ccacacataa cactttggtg gagactaaac | 240 |
| aggatggtgg tctctttgtc cttctttcaa ggcctcctgg aagacttact aagcaaagcg | 300 |
| gggattgctg gggagatgta tcaaggtttc tatacacgca agggcattgc tcggccctgt | 360 |
| ggctgcatct ggttttcatt gccctggctc tcaagggagt ctccctctca ttgagaagac | 420 |
| tcagtggaaa gccttcctag ttgacatagg gtcaagtaaa gacagaatgt caggacctgc | 480 |
| agacacagca gagcaactgg gaaacaatac cttaaaaaca aacaaagaaa aatattta | 538 |

<210> SEQ ID NO 9
<211> LENGTH: 6200
<212> TYPE: DNA
<213> ORGANISM: Cricetulus griseus
<220> FEATURE:
<221> NAME/KEY: gene
<222> LOCATION: (1)..(6200)
<223> OTHER INFORMATION: SIVA1

<400> SEQUENCE: 9

| | |
|---|---|
| atctttccca atggtcatgt agggtcagaa gcgcacaagg atcgcctaaa gctcgtctta | 60 |
| cctacaactt acattcagca aagcaggaga agcccgtttc ccagggtgtg aggaaaggcc | 120 |
| tttcacagag ccagacaaaa gtgggcgggc tcatctagtg tacctgcctt taaaacaaaa | 180 |
| cgactgtatg tctgtggcct gcacttgaca ctggggtggc ttagtgacac tgtcctgcta | 240 |
| agcttgggag agtgccagtg ttacctggtg tgtgatatgg atgtcaggac caaggtgtta | 300 |
| taacagctgg actcctacat ttttggtgtc atggagctac agtgtggtgc ttgttcagga | 360 |
| aaagaaaaa aaaatgcagc aagtccttga agacagacc aggtatatca catttcccag | 420 |
| aactaacagt ctaagaacgt acactccaga gctgccaggg atccaggaat aacaattctt | 480 |
| cctgtctcca gggacagagc agcccagaca cacacacttg gtcgcagtcc ctggaaactt | 540 |
| ctccagactg aagcagacag gtcttaatta gcatggcctg tgctcgctgg aacaccaagt | 600 |
| ggccccttga gtaacatgcc ggagtctggg ggtacattag ctagcccag tctaaggaca | 660 |
| tgtctcattg cattttcacc tctatgacaa ataactata tttaaaaaaa aaactaaaaa | 720 |
| gggtttattt tggatgactg tttcatccat ggccagtcat ggccagctcg gtggctagag | 780 |
| ctctatgtga ggcagaagca tcatggtgga gagcacttca tcaggaagga attagagaga | 840 |
| caggggaacc actcacccct caagacgcac aaccaggtct cacctaaaag cccattcagc | 900 |
| catgaactca ccgagggatg gatgaatcca ttgaagttag gccatcatga tccaatcacc | 960 |
| cttcaatcat gctgccatct ggggaatcac gccttcaaca tgggggcct ctgaggagag | 1020 |
| acttcacatt cataccacac cacccaggaa aggctcacac taaacctccc tgagcccatc | 1080 |
| aggtgggtta gagaggtccc tgaggaccaa gcaggaggaa aatcacaata acattcttga | 1140 |
| ataaaacaac cctattccta acccctttgga aagctgccag tttgcttaga agataagcac | 1200 |
| atgtccccct ctccctctaa cacattcacg ttcggaggga agagggagcc ccattcccga | 1260 |
| gtagcaccca acactgaatg atcaatatgt cagaaaaggc ctggtccaag gttgtccata | 1320 |
| ggaactaaat gcatcatagc caaagcttgc caatggccct ggtgcctaac aggcagatac | 1380 |
| acaactttag gctttctaga cagaagaaca cccagtatca aaacgaacca gctgccacag | 1440 |
| acttgaacta gagggagcaa gctcagaact acggagagag agccagatac atcggcacac | 1500 |
| acagaatgag tactccctgt atgagattct gatgccattt ggtgggaact ttggaaaaag | 1560 |

```
agtaagaaaa agctcagtgt cagacatttt acaagcatac tctggctgtg gcccccaact    1620
gaagggaaaa gacagaagaa actatgacat gattacccct ctctaacacc caccggcagc    1680
cagacccagt gaaacccttt ggaagcttgc agggaattgt gggaattctt ggccgggtga    1740
gggggtgggg gtgtcattat cttaatgtga acagcagtcc tggtggtggt tccctagcca    1800
tgttcccgcc ccgtctgtcc cactggattt aagccttaca gtaggagaca gcccatgcc     1860 tccacataga ggtggagcct gttccttaca gttctacaac aggggacacc cccacgggg     1920 aaggaaacac agaaggcagt tgtcacttct acaggtgttt gtcatcaggg ctttaacctg    1980
tacacctact tggcacttgt cctatgctat tcatgttgaa gtcctaactc ctaagacttc    2040
agaatgtgac tatctggata cagccttttg tttattttat ttttggtgtt ttgagacagg    2100
gtcgcaccac acagcttggg ctggcctcaa actcacagag atccgcctgc ctctgcctcc    2160
ggagagctgg gattaaaggc gtgcgccgcc accacacctg gctcctgggt atatatatat    2220
tcttaacgag ttaaaacggg gtccttaggg tggacccgaa ctcaaagagg ttggtgtttt    2280
tatgagatga ggactcagac accccatgta gtttccatct gcagatcaag gaagatgaga    2340
ggcctgcaga gaacccaacg ccttaatctg aggctgtgcc tttgtaatta cagatcccct    2400
aattggcctt ctcccttttcc gaactcggga acgcaaactc aagtactggg actggggtg    2460 aggggtgtgt tgtctcaaaa tctggagaat gctgagcatg cgccaggcct ccctcgcacc    2520
gtgatgagcg caaaactcaa tgcacctcaa caagtcgccc ttaggttcag atagagtgtg    2580
gaaagaatac aggactcagg aggccctcgg caccgctgct gtgccgactg tgtgcaccgc    2640
gttaggagcc gcccaggcag gcagtgccag cggtaaacgc tcacccaagc tcgggctcac    2700
ggacgcagga ggaccgcagg gagagatggg tgccggcacc caccctgctg ctgcgactcg    2760
tcccccggga agaccaccca tcacagttgc taagcgaccg cggagacttt gtgccgcgca    2820
ggcttacaca gagccccggc gcgtaagccc cgccctggg tagcctcccg ctggtttccc    2880
gcgccacacc ctccagagcc cccgcctctt aatcctcggc ctatcccgag tcgtctcgcg    2940
cactaccccc gcccacctcc aactctcggc ctatcccgcg ccgcgccacg cgaagacccc    3000
gccctccttg ccatcccttt ggcctttccc gcgcccctg agttccaccc acttcctccc     3060
tcagcctatt gcgcgccctt gagccccgcc cccggcctct cccggcccta tcgggctccg    3120
cgccgtcgcc agccccgccc ccgccggcgt tgtgagcgcg ctgtgacgtc cgcgccgctg    3180
tggtcagtgt ttggtacccg ctgccatgcc gaagcggagc tgcccgttcg gggacgcttc    3240
cccgctgcag ctcaaggtcc atgtgggccc gagagagctg agccgcgggg tgttcgccca    3300
gcgctactcg cgggaggtct tcggtgagtg cggagttccg tggtagggcg cgcagcgccg    3360
cgccgtggga gaccccaact ggcttgcgcg tcgccatccc cggggggga ggcggcgtgg     3420 gggggtccc cggggagcgg ctccggggga aatgcgagtg tagccgagga ctgtcgagcg     3480
ggagtcggcc ccctcaagtg ggctttctgg cggcagggtt ttgctttgca gtgatggctc    3540
tctggggccg atgcaacgcg gcttacctgg cttagggcga agtttatgcc tgtagttttg    3600
agtggtgcgc tgtgcctttg ggatgtgtcg ttaaagccca ggctgcggaa ttacagactc    3660
cctaatgcgc cgtgtgtgtg tgtgtgtgtg tgtgtgtgtg tgtgtgtgtg tgtagctgat    3720
gggccctttc cctttctgta ctgtggaatg caaactcgag tgctgagacc tcaggggtga    3780
tgagtgaagt gtgaggcctg aacagcaaag cgtcatgcac tcatttaaaa gaaacaaaag    3840
tagacatgac gggagtcttg gcattcgccc ttgatgctag caactcacca ggcagaagca    3900
```

```
ggcggatctc tgagagttcc ggggccagcc tggtctacag agcgagtgcc aggacagcct    3960
ccaaagccac agagaaaccc tgtcttgaac caccccacc  ccccaaaaaa aagaaaacct    4020
aagtataatt ggaacctagc agcctggctc tactctttta aagacttata tcctggagca    4080
cttgccaggg ccagtcagaa ccagccaggt cagggagggg tgctggtttc tggggtgttg    4140
tatagtcata cagtacacac aatttgaggc ctgaaggatg aataccaagc ctcggcctac    4200
actctggact cttttgtggg ccaggagtcc ttgaggagaa agattactct caacatggga    4260
atcttcctat ctccctcttt ttcaagcagg cttttacaat gtatcttagg ctaaccttga    4320
acttaaacac tcctgctgcc tcagcctcct gagtgctggg atgtgcctct gtatctactt    4380
tctatcttaa agcaggaggt ggcacagact gtaactggcc tgataacagc cactccctgt    4440
gacttttgc  tggctgttgc tgctgccagt ttcacagagg ggccctggg  tctgacaggt    4500
ctcccctggc tgtatgtggg agtgagcatt tctggaacca gcacacagtg tagcctaatg    4560
ggaagcccct gttaaagccc acttagcgct gggatagggg gtgggtggac ctggaaggtt    4620
ctgggagacc tttgtcagga ggttgctgtc tttgtcccct atagtaagtg cagttgtccg    4680
ctggcctgat ggtgattgta ggcgctgttt tgaacctgtg tgtttcctgc ctctttgggg    4740
cacttgctct ggagagtgag tggttcaagg ccagagcttt tctggcgtg  aaagacaggt    4800
gcttatagga gggtgaagag taagacacta acccagtgaa gtaaggttag ctgtggctgc    4860
tgagataggc taatgaagg  aaccctgcgc ccagcacatc ggggtggtgg ggttgggctg    4920
cagcatctgc aggctgctgt ggaaggagcg aacagtggag acagaaagga cgggagcatt    4980
ttcagcttgg aggcagggag gccctggcag tgtcaccact tagggaacag gcacagagga    5040
cgacgcctat gcagggggctt tgcagttggc agtgttgtct ttaggaagga tctttcttcc    5100
ccagaaagaa ccaagcagct ccttttccaa ggggcccagg cctgtagaga ccacatatgg    5160
ggtgaaagat gtcccatcat ccacctgccg gagtcactga agcctggcct ggtgggggcc    5220
cctcaagctg caaggggaca gatgctgatt ggacctgatg gccgactgat acggtgccca    5280
gctcaggcct cagaagctgg tgagtggctg ccagcggtac tcgctggtta tcacacctag    5340
gaaacacctt ggcaaatgct ctcttcaggg gctttgacaa ccttggcaag tagcatccgc    5400
ttagagcagt ggttctcaac tgggtcacga ccctttagcc aatctgtctc caccacgaca    5460
tgaactatat taaggttgc  agtgtcagga aagttgagaa ccactgactt tgaacctggt    5520
aagttgagca aatggcagaa ggtttggaag cctcctgttg ttgggaggtc tgcccctcag    5580
agacatccag gagtggaagt cagcagcttc cagttgttgt atcggaaaag gaacagggct    5640
ctcctggtat cctgtctgta gtaggaacat gctggtccat tgcctgtgga aaaatgagct    5700
catgtgactg gtgaaggcag gcctctgtgt cagcgctaaa tctggctggt cccagaaacc    5760
tcctggctga ccagcaaaac agggaaccat atcttgagac ctagacagag acacagagtt    5820
ctgatagagt actccaggga agagtgaccc ttccatgcta ggactaggtg ggtgatatgc    5880
cctgggaatg cctcgctgtg gatctttagt gccccaggtg gctgatagtt ataaggactc    5940
agtggctggg gcaggtaggt gcccactgcc ctcgtgttct tccagtttct ttccagtgcc    6000
ggtggtgttt tttcctcaca ggtctgcctg ggacagctcc catcgcttgc tcatcctgtg    6060
tgagatctgc agatgggaag gcggtctgca gccagtgcga ccgtgccctg tgtggacaat    6120
gtatatacac ctgctggggc tgcggtgcct tggcctgcat gctgtgtggc cttgcagagt    6180
gagtgctctg acctgtgggg                                               6200
```

<210> SEQ ID NO 10
<211> LENGTH: 199
<212> TYPE: DNA
<213> ORGANISM: Cricetulus griseus
<220> FEATURE:
<221> NAME/KEY: gene
<222> LOCATION: (1)..(199)
<223> OTHER INFORMATION: SIVA1

<400> SEQUENCE: 10

| | | | | | |
|---|---|---|---|---|---|
| gccctccttg | ccatcccttt | ggcctttccc | gcgcccctg | agttccaccc | acttcctccc | 60 |
| tcagcctatt | gcgcgccctt | gagccccgcc | cccggcctct | ccccggccta | tcgggctccg | 120 |
| cgccgtcgcc | agccccgccc | ccgccggcgt | tgtgagcgcg | ctgtgacgtc | cgcgccgctg | 180 |
| tggtcagtgt | ttggtaccc | | | | | 199 |

<210> SEQ ID NO 11
<211> LENGTH: 6200
<212> TYPE: DNA
<213> ORGANISM: Cricetulus griseus
<220> FEATURE:
<221> NAME/KEY: gene
<222> LOCATION: (1)..(6200)
<223> OTHER INFORMATION: SYNE1
<220> FEATURE:
<221> NAME/KEY: misc_feature
<222> LOCATION: (4064)..(4073)
<223> OTHER INFORMATION: n is a, c, g, or t

<400> SEQUENCE: 11

| | | | | | |
|---|---|---|---|---|---|
| atgttggaaa | tactctttga | gcaggtgggc | ctggtggtat | ggacctgtca | tctcagccac | 60 |
| tggtgagcct | gaggtagaaa | aatctcatga | tcaaggtctg | ctaggctaca | caagtgagtg | 120 |
| caatgctagc | ccaggcaact | tagtaagacc | ctgcttgata | ggaagagcaa | agcaaacaa | 180 |
| gggtgggagt | ggggaaaata | gcagtgaact | gcttcctttg | cagcactgca | aaagtgaaga | 240 |
| aggaaaagaa | atacttcttg | aaatgctaat | tctactagtt | agtatacaaa | ataagttgtg | 300 |
| gaactcaaaa | gcatttagtg | tcttttcttgt | acagcattat | taagaagagc | tcagtatttt | 360 |
| tggcagcgta | ggaaaaacca | agtgacaaat | tacttgaagc | cagtgattat | tgtctattgg | 420 |
| cattgacaca | agcagtttca | tttaaatgac | agcccaagag | atcagtttta | ctctaagtgc | 480 |
| gttttaaagc | ttagagtggt | tctttagaaa | tcaacatttc | tcaataaaat | catcctgatt | 540 |
| ttggggatgg | aatgttaaaa | ctgtacataa | atgcactcgg | tgctttggtt | ttgggatccc | 600 |
| tttgtgttga | ataacacga | aaagttgggt | ggacaggggc | aaggagtcct | aactatacca | 660 |
| ggcactcaac | tctgagcagc | tctctccccc | agaatcttat | ggtccagagg | ttggtcatgt | 720 |
| gaaaagtatc | ccaggcttgt | gccatcatct | agagccggag | tttgagaggg | ttgtgagcca | 780 |
| tcatgtgggt | gtccagaggt | gaacctgggg | tgtctgagg | tgaactcaaa | gattttctgc | 840 |
| aagaccagcc | attgatctca | gactttctc | cagccccttt | tcctctcctg | tttcttttag | 900 |
| caagtcttct | atttcaggag | accttgacct | gcagggatgc | ccaggacctg | cacatttcaa | 960 |
| ggggccattt | ccttctcagg | tcagagtggc | tctgttgcca | ttaccatttt | cataaccatc | 1020 |
| ccatttttaaa | tttcctaggt | ctccttaaga | cgacagcaag | tgagtgaacg | actgaacgaa | 1080 |
| tgggctgtct | tcagcgaaaa | gaacaaggag | ctgtgcgagt | ggctgacgca | gatggagggc | 1140 |
| aaagtctccc | agaatggaga | catcctcatt | gaagagatga | tagaaaaact | caagaaggtg | 1200 |
| agctgtggag | tgccttcgag | agtatccaaa | ctttagagga | ggagctaaaa | tagacatata | 1260 |
| aaatctatct | tcatttattt | tttaatttac | ttttggtgtt | tttttttttt | ttttttgcatg | 1320 |

```
tgcatgtttg tatagtgtgc atgcatgtgt gtatgtgcct cttcacatgt gtgtggcacc    1380
ccggatgagc atgtgcttat ggagaccaga ggtcaaagtt aggcatcttt ctcagttgct    1440
tttagtcttt taaattgatg tggggtatct caactgaacc catagctcac agatttgcct    1500
ggtctcccta tccacttggc cagggatcct gttttcccct tgttgcccag gggttacagg    1560
caagggagtc ctcctggtca gtatttgcat gggctcttaa gaaccccaaa ttccagacct    1620
catgtttatg ctctacctga ggagccatct tctgtccttt attattttgc tgagatacta    1680
tctgctgtat aacatgtgtt ttttgacctt gagtctcaac actgatccta aaaactggat    1740
atgtcttctg gtttagtctc tgttgttccc tgcaaataga tcatataaag tgccccccc     1800 cattttttcc agacagggtt tctctatgta gccctagctg tcctagaact cactctgtag    1860
agcaggctag actgggactc agagagctgc ctgcctctgc ctcctgagtg ctgggataaa    1920
aggtatgtac catctctgcc tgtctaggcc tgttattttt aaccagtttt taagaagggc    1980
tagcaaagag actgaataaa acgagagatg gtgtgagacc cactaacttg gtgaaattag    2040
ttcattatta atagaactgc aaactaattt gtcatgtgtt gcagtgacaa gtctctgtgt    2100
ctacctgttc actgaaaaag aggcttccat gattaaggct aagaatacca tttgtctaaa    2160
tatttagaaa aataaatatt tagaaggtac tttgaccttg tgacaatttt tctaaataaa    2220
agttttcagt tgtaccatct cccccaacct atgaccaacc cagctgtggg ttttgaccat    2280
gtttacatta tccgacatgg actccttcag aatggccctc aaattcagca agttggttac    2340
ctccatggca gtaatgccac tactgcacat gctacctggc aggttggtct tacagttcat    2400
agagttaact gtgggtgatg cctcttctct cccataaacc tgcatagaac cttctaaatc    2460
attgaaagtt aattggcagg gaagaagctt atagctcagt tttagcaacc aaggtatgtg    2520
gtgtcttcag caacagctct gttctctctt ctcgtctcca ctactggaga gatggccaga    2580
gctcgtttta ttttaaggac attttttgact aataaggttt cccagcccag gattgggatt    2640
ttcattccat aacctacagc tcctaagaat aggtttcttt ttcagctaca ttcaaaagcc    2700
attttcaaaa ttttgttagt ttttttaaga tttaatgatc atgcttttgt catatgcacc    2760
tcacccatca actcttccca ggtctactcc caattcccta attgcctaac tctgtgtctt    2820
ttttttcacc catcaaggca aatttgtgct gcccaaataa tcttggtgta tagtcttctg    2880
ctggagcaac gtcaacttac caaggactat aatcttagtg aaaacaatct cttcctttcc    2940
taacagctaa caattggtaa taactccaca acttagggta ggattttgtg tcaagctctc    3000
atgaaactct tatttttttt tattatattt ttacttgggt cataacctct tcatttggt    3060 tgatcctttc ccttaagctc tcatctcccc tgtccttcca cccttgcctg cttaagcctt    3120
tccaccccca gccttctctc tacatttaga ctgccttcat ttttactctc ctccctccat    3180
taagaccttc ctctccccat gtaagccaca atatactggt ctcaaactca ctctactgga    3240
agatcttgaa ctcctgattc tcttgcctct acttctcaag tgcagggatt acagtcatat    3300
gccatcatac caacctagtg ccctacaacc aagtgcctta caattccttt cagaaaatcc    3360
attggaataa ttgagactgg acttcacatt atcaagagca ataggcacta ttaattctag    3420
actgatgttc acacggtgtt cctcaggccc aaactgtcca aacagtagaa actgtaatta    3480
gtgtgtttcc agaggagcca gatgaatgca ttaagaatat gccttctgac ctccgtgatt    3540
gctttcatta tgcaggatta tcaagaggaa attgctgttg cccaagagaa caaaatccag    3600
ctccagcaaa tgggagagag gcttgctaaa gctagtcatg aaagcaaagc cgctgagatt    3660
cagtacaagc tcggcaaagt gaacgacagg tggcagcatc tcctggatct cattgcggcc    3720
```

-continued

```
aggtaaatga caccaggtgc aataggatgc ctgcagtggg gatgtcaatt agtcctcctt    3780
catctcagct agtgcagttc ctcctgctgt gacctctccc caaactataa aattagtttg    3840
ttggtgctct gtaagtgtaa ttttgctact gttgtgatgt aaatatttac tgttaaatgt    3900
aagtatgttt tggaggtcat gacccacagg ttgagaagct aaagggaatg cagcacctat    3960 ctcccttttct gagtgactgt actgcctggg gtaacactgt gctcctgctg ctcccatgaa    4020
tggcactttc attaacttca aaagaattta gggagaggga aagnnnnnnn nngggtttt    4080 catttggggg ctttgtgggt atcccaacat ctatggagga aaaagaaaa agccactcca    4140 tcaatatttg taggtgttct tatctggggg gcaggggag gcggcaaaag agctaccaca    4200
tccctgttat gtgtgtagtt agttgggtgt gggcgtgaga ctgacctttg tcattctact    4260
tattcataaa aataaacagc ttcattattg tcaactttct gctttgccat aacagtgacc    4320
ataattagtg gtcttgtgtt ggagaggcag attatattcc atttattctg tagacaggaa    4380
gtgtgaataa aagggatgac aaacagagga aaaacatatg agggcctttg ccatcatttc    4440
aaatgctggt atgacttgaa gatgcacaag gatatttttat attaaaagag taactgacca    4500
tggaagggct tcattttaag tgtaccttcc ttcatgttgg gatgtcaatg ccaagagaca    4560
gctttgtcca ttgactcatt gcatatcaaa agtctgagaa taggggctgg agagatggct    4620
caaaggttaa gagcactgcc tgctcttcca gagatcctga gttcaattcc cagcaaccac    4680
atagtggctc acagccatct gtaatgagat ctggtgacct ctctggcctg caggtataca    4740
tgcaggcaga acactgtata cataataaat acctaaataa gtctttaaac aaaaacaaaa    4800
gtctgagaat agtagctggt gctggggtgt gactcaaagg gagaagggtt gagtagcatg    4860
tgcaaggccc tttgtctata aagtaatttg agtgtcacaa agactggaag gctgagaatg    4920
aatgccacca tagtgggcct ccttgctgga gtatatggtg gcagtgcaga catggaaaaa    4980
aattgagcga aaccattgag ctccctgctc agggacatgc agggaaagga atacatcttt    5040
actgaaatta ccctacagct gaaatgcaca atggttctga atcccaatgt gatgtttagc    5100
ctcacatctc agccaccaag atcataacaa agtcttattc cagaagcaga aattgaaacc    5160
tcgtgtgcta taaattccct tcttggagag acctccccct gggtcaatac cgtggggatt    5220
tttgtgtgtg tgtcagatcc tgactcatgg accaatgtgc ttgtccgtat aactccatca    5280
aattggttaa atttctctca tgaatcccag ggccacagtg atatgaaag ggaagactca    5340 ccatgccaaa aaatatctca aataggcttt aactcagaac agttgtaggc agctggctta    5400
gtttctgctc agctgtcagc taacaataca tggagcacaa tactatctct tcaaagtcat    5460
gcttatttac aacacatctg tgtgacgttt tttcaggtga aattttctta gatattgttc    5520 tctttttac catccccaaa gatatacaaa caaacttgag tcagcagtat gttgataaga    5580
aatgggtggt tttcaccata gtatctaaga cagaaatggg tggttttcac tgtagtatct    5640
aagacgttca tctatgacca catttttagaa tgtcatcatg cagataaatt cctgtgggga    5700
actttggtat agctatagtg ttcatttcta ggtaccacct ataaagttag agcagattaa    5760
aggctgatcg tcagcttgct ctggagtctg aagccacact ggattctgtc tgcctttcag    5820
cttctcccag aagacacttg gctatcacat ttgcttctg tttccttgtt actgtgtgca    5880
ggcggggtgt acttcctcca cacctgtctt tagctatgaa ctggcagctg cttattcagt    5940
ctcattcatg cctctccctc tctccagcaa aaacagtgac tcatgacaca gaacagaacc    6000
tggcacatca catactttg gagttcttca aaaatttaa attatattta tattaatata    6060
```

```
tatatatata tatatatata tatatatata tatatatttt acacagcttt cttcttccaa    6120
gaatggaatt cagatcatca aaggcttggt agttgccttt acctgctaag ccatctcact    6180
gtacccttcc cctcttttct                                                 6200

<210> SEQ ID NO 12
<211> LENGTH: 199
<212> TYPE: DNA
<213> ORGANISM: Cricetulus griseus
<220> FEATURE:
<221> NAME/KEY: gene
<222> LOCATION: (1)..(199)
<223> OTHER INFORMATION: SYNE1

<400> SEQUENCE: 12
atgaaactct tattttttt tattatattt ttacttgggt cataacctct tcattttggt       60
tgatcctttc ccttaagctc tcatctcccc tgtccttcca cccttgcctg cttaagcctt     120
tccaccccca gccttctctc tacatttaga ctgccttcat ttttactctc ctccctccat    180 taagacctt ctctccccca                                                  199

<210> SEQ ID NO 13
<211> LENGTH: 6200
<212> TYPE: DNA
<213> ORGANISM: Cricetulus griseus
<220> FEATURE:
<221> NAME/KEY: gene
<222> LOCATION: (1)..(6200)
<223> OTHER INFORMATION: Smarcc1

<400> SEQUENCE: 13
gacatggacc ttgtttgttt tgatgtgcag aatccttata aatctcattt aatttgtatc      60
ttctatcaga aatgcttttt cttttcacta atttcaggac atatataaat agcaggatgc    120
caagaaactt tcctactcaa tgtcacaggg gtcttagagg cagaagaacc aggttttaca    180
ttcttgattc tgataatatt agaaggaga ttagtatgaa agtgaaaata cataattact    240
acatcctaca cagagtgatc tctttgtccc ctgtaattga gcagaaagac cctggacttt    300
cctatgtgtg gcactgactt tcagtggtaa tttctgcatg aggaggtgag tcaaatatac    360
tatttcccaa tatattacac aggttgttgt ttgtgagtat ttcctgtata gttacataca    420
aaaataagca gaattgttgt ggagtaataa aatgtacaat gtttgtggta aatagctccc    480
tgaagaacac tgtgctacac ctattttgta aatcaatagt ttcctacttt aagtgcattt    540
ctcagtgata tcaagaaact gctgtgtgat gggctctcac cacctgtttc agaagcaacc    600
atggagggga ttttaagata cattctgaag tctataccctg tggttcaatt ctcagaatgt    660
aattttaatt acttttctaa aatcctgtga gaactgcatg catatataca atgaattttg    720
atcatttgta ttcctactct gccctccaac tactcctaga ccatctccta ccacctccat    780
aatcatgaca tctagtgcat gtacataagc ctgcacactg aagcatagaa aaatctacca    840
gtgccacagc tctcaagaaa cttgactctt tgtaccccaa caggtgttag ctgtcaaaca    900
ggtcctcaga tatgtgtagg gcctccataa tccactggga ttttaattgg ctttatcttg    960
tgttggtttt gtaaaggtga tcacagttgc tcagatttta aagttcaag ggcccttgg    1020 tgtgcaaaag ataccatttt gcagcagctc ttcctaacct ctgctatatt ttgaaggaag   1080
aagccactgc aaagagaatc agtgataacc ccctaccaat gtcagtaact aaccatgaat    1140
taaagtaaca aaggacaagt agcatcagca aatcagatca gcttcagcca atccctaagt    1200
atcacattta tgtccttgcc cttctggaaa tttctgagaa gtaatcaaaa agtatgtaac    1260
```

```
ccaaatagga cagcatttct tccacccttg tcccagacct ttgtccttcc taattttatt    1320
tggaatgagt taaatattaa agattacatc cccagagcac acatccttta caggaaccca    1380
tcaatgacat tctgtaaagt gagacaagac taatatttaa acatttcttc acaccaaaca    1440
ttatttacac atacctaatt aagaagttac agcatttcac atccttccaa aatcccttag    1500
cttagtagac aaataatacc taagtccatt attaacacac gattttttaga aaatctttac    1560 ccttatcaaa tgataaatta ggatctaaaa tcatcctaat ttatagaaac aagtcagcat    1620
ttgctatgat tgtgttagtg acaccatgtg aaaaaaatat gctagaaagt ttaaatagat    1680
cgagaatgct ccaaattcag taaatgtaca gctgcttcaa atccatggtt taattttatc    1740
ttcttcaccc ttttagcatt gaatcctggg actcttcagt tcagacacct ttgcaggtgc    1800
tccacaaaag taacctttca atcagattaa ctgccagact gtgacatttg atgtgtcata    1860
atataaggct ttgtgaattt taaatggttc agcacatgaa gctgagatac agaaaagagt    1920
ttgtaaggta taatttaaag actaattagt aaaaaaaatg tattatatac aattaaatga    1980
tgtaattatg aaatagttga tttgccagac atggtagcac aagtttatga tcttaccaca    2040
caggagaatt aggcagaagg aacaagcatg taagactagc ttctattaca caagatttgt    2100
ctcgaatatg atgaacttcg actatgccat tatgactgtg tacctactga gaaaaagaat    2160
tgcacaaact tcttaattct atgggaaatg gaacaatgat tataaatataa ttttcaaacc    2220 tgtttggaaa tatttggaaa tgtaacttcc tatatgccat ttgtatatta attgtattct    2280
agttaataat ctgttttttt gaagtagtta tgggccagta agcttaacta cctgaataaa    2340
gaacttgaac aggaagtcct tctcttttgt tcttttgact tcttcaatat tggaacaaat    2400
gttccccagt tttcctgaca cagagactct tgcatgtgga tcatggtgta gtaaatgcaa    2460
agtggtcttg gatgtctgaa tttgcttgga tgatttgtat aacattgtca cactctatat    2520
acggatccca gcaagtgggg atagtgctac aaagccttcc taacattgac ctcaattcat    2580
gaatgcaatg agggcaaaag gtaagagtca atacaaaact ccgtcaaggg agttttacac    2640
cctttagaaa ccatataaag gaaaaagaga gccaattcca tcaaagctgt cttctgactt    2700
ccccacaaca catatcatgg catgcacttt tcttgctttc cccatcatac acattccact    2760
aataaataag ttaaaatgta aaggatggtg attttccaag gtcagaaaaa taatcactgg    2820
aatatcagaa tgatcatttg ttgaaaatct gtagtaataa tacctcaaac agaagcaaac    2880
caacatctgc agttgcttct cttaatagta aaagtatgta atgttatttt gcagtagaag    2940
acaaaatata attttgtgct ataatttgtt ggtacttcat gagagctcag aaataggacc    3000
taaaaaagac caaatggaaa ggtaggtgga cataagaaag cttatgcaga gttcttcaag    3060
gagagccaag ctgtgtgttt acattgtgtt attctatttc ttggaggttt agcagtgaaa    3120
taacaacatg agacaagaaa aatagctttt tatcagtaat gatagattgt ttgaagagtt    3180
atactgtaat atgtacatag agatcatggt atttaattct caatttagca tgaacaaatt    3240
aagtccattt ttaaaaaaga ggtaatggag gtacagaatg atcacaaatt ctgaggaggt    3300
ttaggaaact ttgtaaggct atgaagctat tgacatgatt taaagactcc tcatggattt    3360
agaatgtaat tttctcagac tcatggatat ttgttgcagt cattctacac tgagcagggt    3420
tggtggtgac atcaggaaca cacagaattt cagacctgca gaagacgcac ggcatgttgt    3480
gtctgtcttg gtactagtgg taacctccag tatccactct ccagaaccaa tatattattg    3540
agttgagtta agcatccact ttcatatttg gaatagaaac tcattcttcc tcccactaag    3600
```

```
acaaattcct taaaagtaac attatctttc atgttcaact ttttatttaa aattcttcac   3660
attgactctg gtctcaaaag gtacatacat ttttaacata agaaaaataa atattagatt   3720
ttctcctttg caaaattgcc aaaggctatt agaaaaaaag agagaaaata ggcatcaata   3780
aataatacac aaaataatag aaactgaaaa tgttagaaat atgaatagat gtttatttct   3840
tggtaatatg ttcagactgg gcactttgta atatctagtg aacctactct gtctaatagg   3900
acagattgtg aagtcagaca atctggatat atttaaattt taactctacc tctaactaat   3960
atttcatgtt ggaaaaattt caaaataact acgtaacagt tttctcatat ataatggaac   4020
tattgggcca tttctgtggc ctcatgagca tacaaaaatg ataccttttt agttaattat   4080
ttgtcataat tattgaaaaa taatttaagt atgtactttc caaaccaaca ctatattctc   4140
taaaggagat tcctatatta ggttcagcac aaaaaaaatc ttgagccaaa ccctaatact   4200
atgtaacatt gtaccctgta tgagccattc cctttgatga tgaatgtaaa tttttatgaa   4260
ttattggttt cattacaggt taaagaattt taatatgaat tggtagctga tttccaaagt   4320
aggtatacaa aaccaaaagg agaataaatg attgataatg aaaatctagt tacttgggat   4380
tttaccaaaa gaaatacttg aaaagaaaat aaagctaaat taatgacaga gacaagtact   4440
gtcctatatt gtatttgatt atatgtttgt ggagacatct gttgttaatt atttatatt    4500 attcttaagt ttagtggaag tcatagctgt agttaactcc ttatctcccc acagctatag   4560
atctccaata acacccatct attttatctg taagcagtat gttgaggaga gagccttcta   4620
gctttagaag taacattttt aactgaaaat aaattcttct ctcatattgt atatcctgac   4680 cacatttttcc cgccctctat acctcccagc atccctaatc tcttcttttc cactttccct   4740
ctgtttcctt tcataaaaga gtaaacctcc aagagccaac aatcagacat aacaaaacaa   4800
gatacagtaa gacaaagaaa aagcccttat atcaaggttg acaaggcaa cccaacagga    4860 ggaaacacat tctaacagca gcacataaaa gagtgagaga cacacctgat cccactgtta   4920
ggagtcccac aaaaccacca agctaataac aataatgcat atgcagagaa cctggggtag   4980
ctgcttgcag aaactgtgct tgcctctctg gtctctgtga gcccatatga gccttactta   5040
tttgattcag tgagtcatgg cctctgggtt tcctccattc tctctgacac tgacaatctt   5100
ccctccagtt tgacttttca aaagaaagtt tggcaaccag ctcagtgttt caaataattt   5160
ttaaatctat tagcccattt gcatgagaat tgattgtaga agtttatgct tctctgaagg   5220
ctgtgattta tttgagcagt taatacttgg tacatgatta tttaatatgt tatatgtgtc   5280
ttcttttgtc ttataaaata tatgtcctgc tttacttttt acctggtcaa ctgataatta   5340
catagattat cagatgcaac aaaagttttt gtatccatca gaaattcccc aaaatgaatg   5400
catgtagact tcataaggaa gccttgcttc atttcaaagc actttctgat tcaaaccaat   5460
aaaaaccaaa caaaaaccct ttaataattg tgttctttta ctaactagca tgaagattaa   5520
acttaaaaaa ggatactcaa aatcagatgc aatatttctt caataatatt tttaatcacg   5580
gttcaggtaa gaaaaaaatt gaagattgaa aattaggatt agtgataaag acaatgacta   5640
gagaaaagag gaaagtgatt aaattagaaa ctgtgaatga cagtagcttt gattgtgatt   5700
gacagagaac aaacgagtgt gaaactgctc atctcagtta ctaagcgcat tcaccatttt   5760
tcaaaactac agtaaagata aaccagacag aaaacaaaac tgagctttgt agaaaacaaa   5820
gattaataca aaacaactaa taataaaaaa tagcataaat ggttatggta ggcgagcaat   5880
acacatttcc agtgagtggt ataagtcttc ttactgtcaa tatagaatca gatgcaatca   5940
ttttccttgc tgcaaagatg attctttatg gagccctttaa aaatatatgc atattggtca    6000
```

```
gttttatgtc aactttacac agacagcttc atttgagaca aaggactctt aatagaggaa    6060
atccttcctt aagattagac gataggcaaa tctgttcagc attttctggt ttaatgattc    6120
acatgggagg gtctgacccc atatgagtag tgacagctgg gcgtgtggcc ctacttgtat    6180
aagaaagcag gtcaagcaag                                                6200

<210> SEQ ID NO 14
<211> LENGTH: 199
<212> TYPE: DNA
<213> ORGANISM: Cricetulus griseus
<220> FEATURE:
<221> NAME/KEY: gene
<222> LOCATION: (1)..(199)
<223> OTHER INFORMATION: Smarcc1

<400> SEQUENCE: 14
taaaaaagac caaatggaaa ggtaggtgga cataagaaag cttatgcaga gttcttcaag      60
gagagccaag ctgtgtgttt acattgtgtt attctatttc ttggaggttt agcagtgaaa     120
taacaacatg agacaagaaa aatagctttt tatcagtaat gatagattgt ttgaagagtt     180
atactgtaat atgtacata                                                  199

<210> SEQ ID NO 15
<211> LENGTH: 6200
<212> TYPE: DNA
<213> ORGANISM: Cricetulus griseus
<220> FEATURE:
<221> NAME/KEY: gene
<222> LOCATION: (1)..(6200)
<223> OTHER INFORMATION: RSG19

<400> SEQUENCE: 15
caggacctat atgttggctc tcaaccattt gtaactccag ttccaacacc ttctggcctc      60
tccaggtatg catgtggcac acatattcag gcaaaacatt catacacaca aagtttaaga    120
gccatataaa gcccctttaga ggatgtgggc actactacca gccaacaggg ctctcagcaa    180
tctctggaca gggtgatgct gtggcagagg cacctgtcta caagtagttt cttcttagcc    240
tgtggagggt ctagggaaca ggactgggtc tgagtcctaa aatccacccc atcccacccc    300
tatatgcctc agtgcttctg tatctcttct atgagctgct ccccaggccc ataccatg      360 taccccccagg cctatatact ctggttttgc cctctttgag ccatgtaccc ctgcccaaat    420
gccctggggt cttcttccca gtataagctg caccctttaag gtccacatac caggagcagc    480
tgcagcagca gcaccagcat aagcagcagg ggttgcgact gggggggtcct gaggggggctg    540 catcatggct ggacatcgag gggggcctgt ccgcctcctc tggtcctgtg tgctgaggaa    600
gagggggctg cctcaacctc cattccagaa ttcactggac cctatgtctg cccatctgcc    660
caactggctg tgcccccaag ggcctcaggt gtccaggaac ccaattagag ggaggaagtg    720
cctacctgtt tctccgcctc atgtggggtg ggcatgtgtg ggtggagagg gttgcacaga    780
ttctgtggtg ccagctctgg accttcactg cagtctggga gcttggatct gagaagagtg    840
ttgggagttc tgactgaggg cctgtgacct gggcccacct tgtaacctct gcaaccacct    900
caggtccctc agagggagct tgctcagagc tctaccccaa gtctgtgtgc taaccccata    960
tggaagtgcc ccaggcaatg atggggctac tgcagttggg cctcccacaa agggctctaa   1020
gataccccca tctactcagt ccccaagaag ccggaagcct gggttcctct ttcttggctt   1080
ccggctcctg gcccctccta aggggactgg agctacaggc tggtatggag atggtaggat   1140
```

```
actctgatgg ctccctccct ctaggtaggt gggtagacat gctacccaga tgactgcaga    1200
gggctaggtc tgaggcacca gagtacttga gtagaattca gaacaagact tcctgaaagt    1260
gaggaatgga ggtgggggt tactcgagag atgtgtactt aggtaacaag gctcttaggt     1320
ccttggctgc gtcagacacc cccacttcac cctggtttcc cttttctcc tgaggatgca     1380 gaagcaggga gtgctagcca tggaagctgg ggtggcaatg tgggaggatc agctgcttag    1440
ctggagcctt gggctcttca atgggttttc atatgattta tcattcttga tgtttggacc    1500
acaccttcac agggggttct aggaacctct caggcctctg aaagctgact tcaaattcca    1560
gtgtccccag gaaaaacaga agcaaagcat ccaattagca ccctggcagc agttttgaat    1620
gcctcctctc tccccagcct gtgcccattt ctgaccaggt ggaggctagg ctatccaggc    1680
cttaagatct ctgctctgcc caccttcctc acattaacct ggggctcacg ttactttgtc    1740
gatgaaatcc accctcctgt agccctgaat ccagcagagg gaggcccttt atcctcttct    1800
gcctgaggtc tgtacactga gggcagcccc accacctggc tcgatttctg agatggtggg    1860
ttcccaagtc tcccagcgtg caaaccagga cacaaaagta gcttgggctg tacttccctg    1920
gggtggagct tctagggaaa ggaaggggtg tagtagccta aggtctctag gctctccaga    1980
gtcatcaccc tgcagaccat ccctcagatg ctccatctcc aaccagctga ctggacaggg    2040
aacagcctgg ggtgtgtggg gcctggatgc tggggtccag tttgtgcaga cgcaggtgtc    2100
tgccattttc cccagctgca ggctcttgtc ctggctcctt gcacccatca aaggtcggtt    2160
gggaccaccc atgtcgtcca gagtgctctt gactaccgcc tcccttcttt ctagggaagg    2220
ggagcccagc atctgaatta gggttttcct gccccatctc cggatactgg atggctcatt    2280
ccctccccaa gcctcccagg cgttggcctc ccaagtctat gctgagacca aatgcagcaa    2340
atctggtctc tggggacaga agctccctgg ggaatggctg ccgtgttgct ccacagaaga    2400
aaatgttcaa gcccgaccag tccaaaaaaa aaaaagaac ctttgggggg gggtaacagg     2460
ggttccattc ccacttccat cccacactgt cattgtccta cctgtacctc catggcgggc    2520
cagacctctc tcaccatggc gaaccccgct gcccaagccc acctgtggga tggtaggccc    2580
ccacccagtt actgctttct gctggtgggg tcgtctggag ggctggtctc ttcttcgcgg    2640
tccctctcgc agtctctgac gccccccaccc cttcttaag gaattcgcca tgaggcccca    2700
ctcaccagcg acctaaaggc ggatgggggc gggagggcca ggttcggtct gggcccacc     2760 ctggctgccg aagggggcgtg ctctaaagca gcagggactt aagtcagaca gcaagatgta   2820
ctcctgggta ttcgcgagat aggaaggcgc acagaatccc tctcgggtgg ggctgtggag    2880
ggggcgcaac attcacccct aaggctcgcc gggccgagtg gctagtggac ccaactcgaa    2940
gggtgggtaa ggtggtggat cggtgtctgg cctggcccct ccccactagg ctagcgggcg    3000
ggagacacgg aaacctgggt tcttccggcc cccacccttta gcaattactt ctcaaagctc    3060
tgagctgaag aaaaggggga accttgctgc ggctctccct cccccacgcg caggggtgg     3120 gctccggtcc caccgcgacc caggtccacg tgggctggtc gctgaagtcc gggaacagag    3180
ccggcatcta catctccggg gcccgcccgc ggtccagcgc cgcactcacc gcagagtccc    3240
cgagtcacag cgcccgcgcg atccgaagtc ctgcttgtcg ccggggaggg ggcgcaggcg    3300
cagtgcgcag gcgcctccac ggtacttccc caaagagagg ggccgggact tcctcgagcc    3360
ccagcgcctg ctcgcccgca gtgccccgcc ccgcgcccgc tcccgcgccc cacccgcgct    3420
ggcgtgtcgt cctgcggtag cgtggcatgg tgacctgag gggtgagtcg tacacagaca     3480
gtggattgag ccggcgctcc gtctggttag ctaggttttc ccagcctttc ctttctgtgg    3540
```

```
tagtgcagtg tggggcacca gagctgagcc cagtgtgctt cttggcagga tgagaagagg    3600
cctttgggaa ggactggcct gttgtactgc cctgtccgcc ccacccctte gcatttctga    3660 gtctggtctg tcactctgct gtccacagag aagggagat tcaggaactg cagcttggtg    3720
ggcactgtga atgcaggttc ttatatcaaa ttaccccgaa agtttctggg cctagttga    3780 gtccctccct attgacccct caaattgctc aagatagcc ttttctgcaa atggccttac    3840
tctttggcca gctcttcaga tcctttatta ttgggtgcag atttgaatta gctcattatc    3900
ccagcatgct ctgggcaagt gtccagggc cctgaccta ctttagactt ggtttgtagg    3960
gtgtgtgtgg ttgcttgggc catgcggttc ctgccttct tagcactgga acacagccta    4020
accagttcag gtgctagggt cttggaagaa aaaaaaaaaa aaaaaaaaaaa aatttaaaaa    4080 aactttttaa tcgcacaggt tgtatatgct gaccacagaa gttagaggtg caaagcaaat    4140
acccactctt gaggcagcgg gtcccaggca gacagactga cctggagcta actgcagtgg    4200
actagaatgg gagacaggcc caaaggat gggtgagag gtgaggaggg caggatgttg    4260
ccatgatgtt cagggagtct ggatgaagag agaacattgg ttgagagcct gaggctacca    4320
ggctttctct aatgctgtgt ggggcttgat gaaaaaagcc agaaccctt agctgccacc    4380 tgatggattc caaagcaagg tagaggctaa gaagcccatc taaacagtag tagttgcttt    4440
agataatagt cctgagaagt ggacacagtt tagaataagg aggcccagta gaaatgggtc    4500
aataccaggt ggagacaaca aaacaaagct gattctgcag tatttggtgt gggcaactgg    4560
ctgtgggtag aagtcagtat gcgttcttcc cctcagttca ttttacatgc ctacccactt    4620
gttctctgct accttacatc tgttctatac tcaattagca tctttaagca cagagaatgc    4680
ccctaaatct aggcaggaga ccaggagcac tgagcaagtg acactagtga ggatggaact    4740
ttaacacaat ttacccttt ctagagcagg acccctactc ccagcccac ccccccaccc    4800 cggcaccagc cactcataag cccccacttaa ctgtgcatgg gccacaggct ttgtatcctc    4860
gttggatttt cttcagacag agggatcctg tgccaccttc cttagcctac tctgtaaacc    4920
caatccctca ctgatgtgga gatcaagtgg cactcttaag ctggtctgac acttggtgta    4980
gagctctttt gccattgtta tgctggcctt tcaggatgt tggtgtgtgt gtcctcagcc    5040
ctctgctctg aggtacttat ctgaattact cactatgtgg gacactgcgg taatcttaga    5100
catctctgtg atcaccatga agaaatgcag ggttggaaaa gtgactttac taaatagatg    5160 aagttttttct aggctcttgg caaatccttg gcaagctcct ctacaaggag cttgaccaga    5220
ggagcccagc attggctatc atctggtgta attgactgtc attagaagac tacaatctgg    5280
gtgtgtgtga ccatcattcc tggatgaaga gactgtctcc ttttccctgt ctacacccat    5340
gtccaaacct accatttccc tgctctgcca tcctccccat tgcctgaaac cccctcccct    5400
cctcctaaga gctgctgctg atttgtgagt gctcccatct gggtttggat caaggcccag    5460
ggcagcaaca ggccagaaag tgagaagggt catgcgcagg gggagaagac cagctgagga    5520
aacagagccc tgggaactgg ccatcagtga gtaagagctt tctggaccac agttttgatc    5580
tcttcttcct ttctgttctc tgttccatga agagccaggg ggagctccca tgcagggaca    5640
gggagctgtg tacctcccca tagtttctgc ctctgtccag cctgctgggt agggactaag    5700
aagaaggaca aggccaaagg actgaagggc aagagaccac aggttctgca aagaacccat    5760
gctgtggaga agaggaagaa gagcctccca gaaaccgggg gcttttcaga gtctagtggt    5820
cagaacggga tgagtggctt acttcctgtg ctccatattt ggtggatgag tgagcacagg    5880
```

```
aggctgtttc tgatgaaagg gaggctgtgg gtgagtcttc tgtcccacca tccagggacc    5940
ttggtgagga gcaccctgtt cacaacctgg tggtcctctg ggcatgactg gactctccaa    6000
aggtgagctt attccctctc ccagaatgcc accccagtct tcagatggaa tgatcctaat    6060
ttaggagaca gccctgattt ttgtgggtgc tggtgtctag gcaggctcat tcatccctat    6120
tcttttccac actagttcac gccctccccg catctgtggc tttgaagggc acccattacc    6180
tgatgggggc aggtggtttg                                                6200

<210> SEQ ID NO 16
<211> LENGTH: 199
<212> TYPE: DNA
<213> ORGANISM: Cricetulus griseus
<220> FEATURE:
<221> NAME/KEY: gene
<222> LOCATION: (1)..(199)
<223> OTHER INFORMATION: RSG19

<400> SEQUENCE: 16
ggagacacgg aaacctgggt tcttccggcc cccaccttta gcaattactt ctcaaagctc      60
tgagctgaag aaaaagggga accttgctgc ggctctccct cccccacgcg caggggtgg     120 gctccggtcc caccgcgacc caggtccacg tgggctggtc gctgaagtcc gggaacagag    180
ccggcatcta catctccgg                                                 199
```

TARGETED INTEGRATION SITES IN CHINESE HAMSTER OVARY CELL GENOME

CROSS REFERENCE TO RELATED APPLICATION

This application claims priority to U.S. Provisional Application No. 62/436,714, filed on Dec. 20, 2016, the content of which is hereby incorporated by reference herein in its entirety.

INCORPORATION BY REFERENCE OF A SEQUENCE LISTING

A Sequence Listing is provided herewith as a text file, "2019-06-20-319-sequence-listing.txt" created on Jun. 20, 2019 and having a size of 71, 110 bytes. The contents of the text file are incorporated by reference herein in their entirety.

BACKGROUND

Chinese hamster ovary (CHO) cells are commonly used for producing therapeutic proteins with proper posttranslational modifications such as glycosylation. Traditional random integration cell line development (CLD) method for generating high-producer cells is a time-consuming and labor-intensive process that requires screening of many cells. A basic goal in the development of cell lines for protein expression is to express the protein with high productivity and stability over many generations. Targeted integration (TI) of a transgene into an active and stable chromosomal region is desired for stable expression of recombinant proteins. Ideally, the expression titer and stability of a target integrated cell line should depend mostly on the integration site. Hence, it would only require screening hundreds of cells for high productive clones by using TI-CLD strategy.

SUMMARY

In one aspect, provided herein is an engineered cell. The cell contains an exogenous nucleic acid molecule inserted in the genome of the engineered cell, wherein the engineered cell is obtained by a process that includes introducing into a host cell a construct for inserting the exogenous nucleic acid molecule into a target site within an expression-enhancing sequence in the genome of the host cell, the expression-enhancing sequence being at least 80% identical to a sequence selected from SEQ ID NOs: 1-16 or a fragment thereof. For example, the expression-enhancing sequence can be selected from SEQ ID NOs: 1-16. In some embodiments, the construct is a homology recombination construct that includes the exogenous nucleic acid molecule flanked by a first homology arm and a second homology arm, the first homology arm being homologous to a sequence upstream of the target site and the second homology arm being homologous to a sequence downstream of the target site.

In some embodiments, the expression-enhancing sequence is selected from SEQ ID NOs: 2, 4, 6, 8, 10, 12, 14, and 16.

In some embodiment, the host cell is a CHO cell.

The engineered cell can contains the exogenous nucleic acid molecule at the target site. Alternatively or in addition, the engineered cell contains the exogenous nucleic acid molecule at an off-target site, wherein the engineered cell expresses a higher level of the exogenous nucleic acid molecule as compared to a control cell.

In some embodiments, the exogenous nucleic acid encodes a polypeptide.

In another aspect, described herein is a method of producing an engineered cell that contains an exogenous nucleic acid molecule. The method includes introducing into a host cell a construct for inserting the exogenous nucleic acid molecule into a target site within an expression-enhancing sequence in the genome of the host cell, the expression-enhancing sequence being at least 80% identical to a sequence selected from SEQ ID NOs: 1-16 or a fragment thereof, whereby the exogenous nucleic acid is inserted into a genomic site in the host cell to produce the engineered cell. The exogenous nucleic acid can encode a polypeptide.

In some embodiments, the construct is a homology recombination construct that includes the exogenous nucleic acid molecule flanked by a first homology arm and a second homology arm, the first homology arm being homologous to a sequence upstream of the target site and the second homology arm being homologous to a sequence downstream of the target site.

In some embodiments, the host cell is a CHO cell.

In some embodiments, the expression-enhancing sequence is selected from SEQ ID NOs: 2, 4, 6, 8, 10, 12, 14, and 16.

In some embodiments, the method can further include, after the introducing step, selecting an engineered cell that expresses a higher level of the nucleic acid molecule as compared to a control cell.

In yet another aspect, described herein is a construct for inserting an exogenous nucleic acid molecule into a target site within an expression-enhancing sequence in the genome of a host cell, the expression-enhancing sequence being at least 80% identical to a sequence selected from SEQ ID NOs: 1-16 or a fragment thereof. For example, the construct can be a homology recombination construct including a first homology arm that is homologous to a sequence upstream of the target site and a second homology arm that is homologous to a sequence downstream of the target site.

In some embodiments, the expression-enhancing sequence is selected from SEQ ID NOs: 2, 4, 6, 8, 10, 12, 14, and 16.

In some embodiments, the construct further includes an exogenous nucleic acid molecule flanked by the first homology arm and the second homology arm. The construct can further include a promoter operable linked to the exogenous nucleic acid molecule.

The details of one or more embodiments are set forth in the accompanying drawings and the description below. Other features, objects, and advantages of the embodiments will be apparent from the description and drawings, and from the claims.

BRIEF DESCRIPTION OF DRAWINGS

FIG. 1 is a sequence that includes positions 1001-5537 of SEQ ID NO: 7. In a randomly integrated clone, the sequence between the two black boxes was deleted and the pCHO 1.0 vector with Herceptin gene was inserted therein. Two PAM sequences are boxed and two CRISPR targeting sequences are highlighted in grey. Two homology arms used for target integration of a gene are shown in bold font. The underlined sequences are primer sequences.

FIG. 2 is a sequence that includes positions 1100-5208 of SEQ ID NO: 9. The black box shows the site of integration of a Herceptin gene in a randomly integrated clone. A PAM sequence is boxed. Two homology arms used for target integration of a gene are shown in bold font. The underlined sequences are primer sequences.

DETAILED DESCRIPTION

Figure 3:
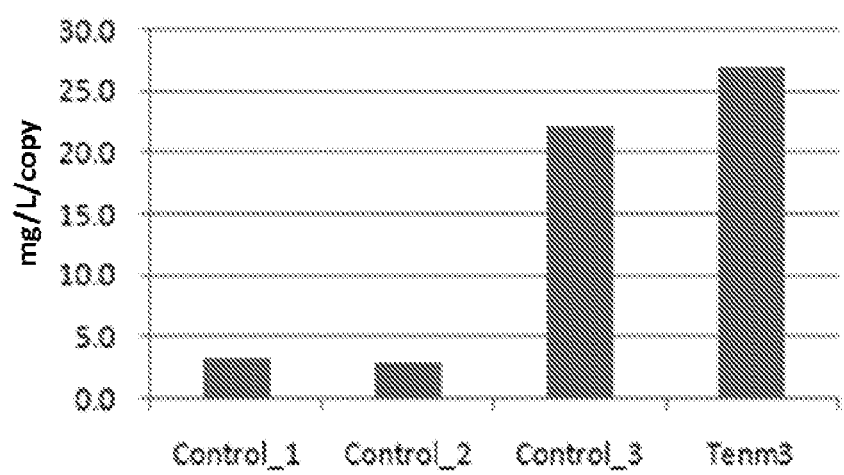
FIG. 3 is a graph showing the expression (mg/L/copy) of a Herceptin gene inserted at a Tenm3 site in CHO—S cells. The graph is based on the data shown in Table 2 below.

It was unexpectedly discovered that a gene inserted at a site (i.e., a target site) within certain genomic sequences in CHO cells exhibited enhanced expression. Further, it was found that a gene inserted into an off-target genomic site via a homologous recombination construct designed to specifically insert the gene into one of these genomic sequences also exhibited increased expression. Therefore, these genomic sequences are expression-enhancing sequences.

As used herein, the term "site" in "insertion site", "genomic site", and "target site" refers to a region including one or more nucleotides (e.g., 1 to 500 nucleotides).

The term "exogenous nucleic acid molecule" refers to a nucleic acid molecule that is located at a site in a cell that is not the natural site for the nucleic acid molecule. For example, the nucleic acid molecule may naturally exist in the cell at a different site. Alternatively, the nucleic acid molecule may originate from a different cell.

Unless otherwise stated, the CHO genome referenced herein refers to the Chinese hamster July 2013 Assembly (C_griseus_v1.0/criGril).

The expression-enhancing sequence can be selected from a sequence that is at least 80% (e.g., 85%, 90%, 95%, 98%, or 99%) identical to a sequence selected from SEQ ID NOs:1-16 or a fragment thereof (e.g., 100-2000, 150-1500, 200-2000, 100-500, 250-500, 200-750, 500-1000, 500-1500, 800-1500, 1000-1500, or 1000-2000 nucleotides). A target site for inserting an exogenous nucleic acid molecule can be located anywhere within or near (e.g., within 500 nucleotides upstream or downstream) the expression-enhancing sequence. In some embodiments, the target site is within positions 1-500, 200-500, 50-1000, 100-1000, 200-1000, 300-1000, 400-1000, 500-1000, 100-2000, 500-2000, 700-2000, 1000-2000, 500-3000, 1000-3000, 1500-3000, 2000-3000, 2500-3000, 500-4000, 1000-4000, 2000-4000, 1500-5000, 2500-5000, 3500-5000, 4500-5000, 2000-6000, 3000-6000, 4500-6000, 5000-6000, or 5500-6000 within SEQ ID NO: 1, 3, 5, 7, 9, 11, 13, or 15.

These expression-enhancing sequences can be used to produce an engineered cell that highly expresses one or more exogenous nucleic acid molecules inserted within the genome of the engineered cell. In some embodiments, the engineered cell is produced by integrating an exogenous nucleic acid into the genome of a CHO cell. The engineered cell exhibits a higher (e.g., one or more folds) expression level of the exogenous nucleic acid molecule as compared to a control cell.

A "control cell" can be a cell containing the same nucleic acid molecule inserted at a different site or by random integration. For example, a control cell can be generated by randomly integrating a pCHO 1.0 vector containing the nucleic acid molecule into the genome of a CHO host cell. The CHO Consortium has also identified various potential genomic sites. A control cell can be produced by specifically inserting the nucleic acid molecule into one of these sites. The expression level can be measured at the mRNA level or protein level. As an engineered cell or control cell can contain more than one copy of the inserted nucleic acid molecule, the comparison can be normalized by determining the expression level per copy.

Whether a target site within or near one of the expression-enhancing sequences enhances expression of a nucleic acid molecule can be determined by a skilled practitioner in the art. The precise location of the target site within or near an expression-enhancing sequence is not critical as long as the site can enhance expression and permit stable integration of a nucleic acid molecule. The site selection also depends on the genome editing technique used to insert the gene.

The engineered cell described herein can be obtained by a process that includes introducing into a host cell a construct for inserting the exogenous nucleic acid molecule into a target site within an expression-enhancing sequence in the genome of the host cell.

Although methods and constructs can be used to specifically insert a nucleic acid molecule within one of the expression-enhancing sequences, off-site insertions can nevertheless occur. It was found that engineered cells containing such off-site insertions also exhibited increased expression of the inserted nucleic acid molecules. Without intending to be bound by theory, it is believed that such off-site insertions carry the homology arms (or fragments thereof) in the homology recombination constructs, which are derived from the expression-enhancing sequences. Therefore, the engineered cell described herein can have an exogenous nucleic acid molecule inserted at a target site within one of the expression-enhancing sequences or at a different site.

Various methods can be used to insert an exogenous nucleic acid molecule at a genomic site. Such methods include homologous directed repair, non-homologous end-joining, zinc-finger nuclease (ZFN)-based method, TALEN (Transcription Activator-Like Effector Nuclease)-based method, and CRISPR (Clustered Regulatory Interspaced Short Palindromic Repeats)/Cas9 method.

A homology recombination (HR) construct for insertion of an exogenous nucleic acid molecule at a target site within or near one of the expression-enhancing sequences described herein can be designed. The construct includes a first homology arm that is homologous to a sequence upstream of the target site and a second homology arm that is homologous to a sequence downstream of the target site. Each homology arm can include, for example, 200 to 1500 nucleotides (e.g., 200-250, 200-400, 250-500, 300-500, 400-600, 450-650, 500-800, 550-750, 650-900, 800-1000, 950-1200, or 1000-1500 nucleotides). The HR construct can further include multiple cloning sites between the two homology arms such that a gene to be inserted into the genome can be ligated into the construct. Alternatively, an HR construct containing the gene flanked by the two homologous sequences can be constructed using techniques known in the art, e.g., PCR.

The HR construct can be used in a TALEN or CRISPR/Cas9 system to insert a nucleic acid molecule into the genome of a cell.

A target site may be selected depending on the genome editing method used. TALEN and CRISPR/Cas9 methods both work by introducing a double-stranded DNA break in the genome at a target site. Based on the selected site, an HR construct harboring the nucleic acid molecule to be inserted at the target site can be designed and constructed.

TALEN utilizes a chimeric nuclease that contains an artificial DNA-binding domain of transcription activator-like effector (TALE) proteins and the catalytic domain of restriction endonuclease FokI. As the code of DNA recognition by TALE proteins has been deciphered, an artificial DNA-binding domain for recognition of any DNA sequence can be designed. To minimize off-site effects, TALEN method can use a pair of chimeric nucleases that each recognizes a sequence on either side of the double-stranded DNA break site. A skilled practitioner would be able to design a TALEN construct directed at the selected site.

CRISPR/Cas9 requires a gRNA specific to the targeted site and the endonuclease Cas9. The target site may be any sequence (about 20 nucleotides) that is unique compared to the rest of the genome and is immediately upstream of a Protospacer Adjacent Motif (PAM). Upon binding of the Cas9/gRNA complex to the target site, Cas9 cleaves the DNA. Two exemplary PAMs within SEQ ID NO: 7 are shown in FIG. 1 and an exemplary PAM within SEQ ID NO: 9 is shown in FIG. 2. A skilled practitioner would be able to design a CRISPR/Cas9 construct directed at a target site.

The exogenous nucleic acid to be inserted can include a sequence encoding a polypeptide operably linked to a promoter that is functional in the engineered cell. The promoter sequence can be endogenous to the coding sequence. In some embodiments, the coding sequence is operably linked to a heterologous promoter sequence. Expression of the exogenous nucleic acid molecule can be further optimized using techniques known in the art. For example, expression can be further enhanced by linking the nucleic acid molecule to a strong promoter and/or one or more transcription enhancer elements.

Integration of the exogenous nucleic acid molecule into the genome of a cell can be verified using methods known in the art. The engineered cells can be cultured under suitable conditions to express the nucleic acid molecule. Whether the engineered cell exhibits enhanced expression can also be determined using methods known in the art, e.g., ELISA, or RT-PCR.

Further, as the expression-enhancing sequences can exert an expression-enhancing effect whether they are at their native genomic loci or at different loci, they can be included in expression vectors for transient expression of genes. For example, an expression vector can contain a gene and one or more expression-enhancing sequences. If more than one expression-enhancing sequences are included, they can be arranged in tandem with or without spacers between them. The vector can be introduced into a host cell to transiently express the gene.

Various host cells known in the art can be used to generate the engineered cells described herein. Such host cells can include any mammalian cells. Preferably, the host cells are CHO cells.

The engineered cells described herein can be used in various commercial and experimental applications. In particular, the cells can be employed for producing therapeutic proteins.

The specific example below is to be construed as merely illustrative, and not limitative of the remainder of the disclosure in any way whatsoever. Without further elaboration, it is believed that one skilled in the art can, based on the description herein, utilize the present disclosure to its fullest extent.

EXAMPLE

We previously generated two CHO cell lines, 3C8 and 3G7, by randomly integrating a pCHO 1.0 vector containing the Herceptin gene into the genome of CHO—S host cells. 3C8 and 3G7 respectively harbor 12 and 5 copies of the gene and produce 3 g/L and 2.5 g/L of the gene product. The integration sites in these two cell lines were analyzed. See Table 1 below. The Srxn1, Adh5, Asphd/Josd2, Tenm3, Siva1, Syne1, Smarcc1, and Rsg19 sites were located within SEQ ID NOs: 2, 4, 6, 8, 10, 12, 14, and 16, respectively.

TABLE 1

Integration sites of 3C8 and 3G7 cell lines

| Cell line | Site | Location |
|---|---|---|
| 3C8 | Srxn1 | SEQ ID NO: 2 |
|  | Adh5 | SEQ ID NO: 4 |
|  | Aspdh/Josd2 | SEQ ID NO: 6 |
|  | Tenm3 | SEQ ID NO: 8 |
| 3G7 | Siva1 | SEQ ID NO: 10 |
|  | Syne1 | SEQ ID NO: 12 |
|  | Smarcc1 | SEQ ID NO: 14 |
|  | Rgs19 | SEQ ID NO: 16 |

The Tenm3 integration site in the 3C8 cell line is shown in FIG. 1. In the 3C8 cell line, the sequence between the two black boxes was deleted and the pCHO 1.0 vector with Herceptin gene was inserted therein. The integration site within Siva1 in the 3G7 cell line is shown in FIG. 2.

We tested the Tenm3 integration site by inserting a Herceptin gene into the genome of CHO host cells using CRISPR. Referring to FIG. 1, the two CRISPR targeting sequences used are highlighted in grey and the PAMs are boxed. The upstream and downstream homology sequences used for integrating the Herceptin gene are shown in bold font in FIG. 1.

A CRISPR vector and a homology recombination donor vector were introduced into CHO—S and DXB11 host cells. The cells were sorted and recovered 48 hours after transfection. Different concentrations of puromycin (10, 50 or 100 μg/ml) and MTX (100, 500, or 1000 nM) were used to selected cells containing integrated genes. See Tables 2 and 3 below. FACS or limited dilution was used to select single cells to establish single cell cultures. Integration of the Herceptin gene into the pre-selected site was verified using the T7E1 assay and junction-PCR assay.

Figure 4:
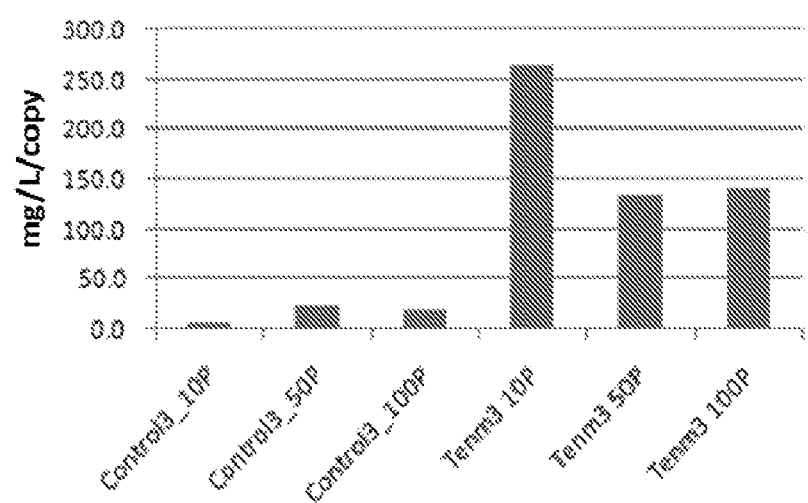
FIG. 4 is a graph showing the expression (mg/L/copy) of a Herceptin gene inserted at a Tenm3 site in DXB11 cells. The graph is based on the data shown in Table 3 below. 10P, 50P, and 100P each indicate the concentrations of puromycin and MTX used to select the cells. 10P: 10 µg/ml puromycin and 100 nM MTX; 50P: 50 µg/ml puromycin and 500 nM MTX; 100P: 100 µg/ml puromycin and 1000 nM MTX.

Expression of the inserted Herceptin gene in the pooled CHO cells selected by puromycin and MTX was assayed using ELISA. We generated three controls by inserting the gene into each of three active integration sites previously identified by the CHO Consortium (control 1, control 2, and control 3). The expression titer per copy (mg/L/copy) of the gene inserted within the Tenm3 integration site was significantly higher than the three controls. See, Table 2, Table 3, FIG. 3, and FIG. 4.

TABLE 2

Targeted integration at Tenm3 site in CHO-S host cells

| Site | Puromycin (μg/ml)/MTX (nM) | Titer (mg/L) | Copy number | Titer/copy (mg/L/copy) |
|---|---|---|---|---|
| Control_1 | 10/100 | 36.6 | 11.0 | 3.3 |
| Control_2 | 10/100 | 24.8 | 8.4 | 3.0 |
| Control_3 | 10/100 | 35.6 | 1.6 | 22.0 |
| Tenm3 | 10/100 | 36.9 | 1.4 | 26.9 |

TABLE 3

Targeted integration at Tenm3 site in DXB11 host cells

| Site | Puromycin (μg/ml)/MTX (nM) | Titer (mg/L) | Copy number | Titer/copy (mg/L/copy) |
|---|---|---|---|---|
| Control3_10P | 10/100 | 16.85 | 2.2 | 7.7 |
| Control3_50P | 50/500 | 219.32 | 9 | 24.4 |
| Control3_100P | 100/1000 | 231.62 | 12 | 19.3 |
| Tenm3 10P | 10/100 | 79.4 | 0.3 | 264.7 |
| Tenm3 50P | 50/500 | 267.24 | 2 | 133.6 |
| Tenm3 100P | 100/1000 | 298.46 | 2.1 | 142.1 |

Figure 5:
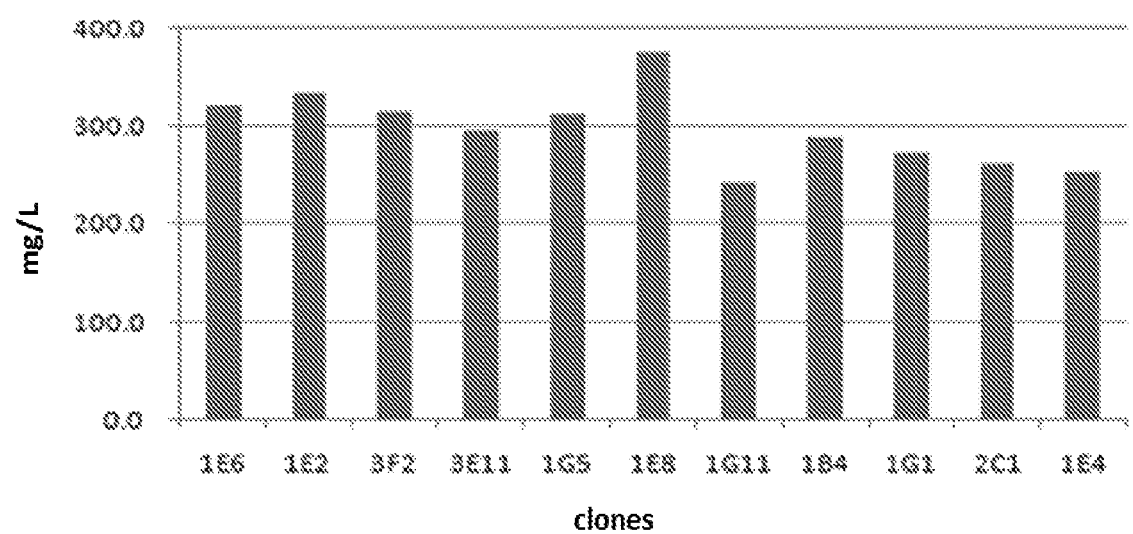
FIG. 5 is a graph showing the expression titer (mg/L) of individual clones of DXB11 cells with a Herceptin gene inserted at a Tenm3 site.

We tested single clones derived from DXB11 cells in 6-day batch cultures and found that they exhibited enhanced expression of the inserted gene. See FIG. 5. In particular, the clones DXB11-1E8, DXB11-1E2, and DXB11-1G5 could be cultured for 60 generations without losing the enhanced expression.

We also inserted the Herceptin gene into the Siva1, Syne1, Smarcc1, and Rgs19 sites in DXB11 host cells using CRISPR to generate engineered cells. 750 μg/ml of geneticin without MTX was used to select cells with the desired insertion. This condition selected cells with a low copy number of the insertion. Despite the low copy number, these engineered cells also showed increased expression of the gene as compared to cells generated by random integration (titer=about 80 mg/L). See Table 4. In particular, the selected cell pool generated by targeting the Siva1 site had a titer of 235 mg/L/copy. FIG. 2 shows the PAM sequence and the two homology arms used to insert the gene into a Siva1 site.

TABLE 4

Targeted integration at Siva1, Syne1, Smarcc1, and Rgs19 sites in DXB11 host cells

|  | Siva1 | Syne1 | Smarcc1 | Rgs19 |
|---|---|---|---|---|
| mg/L | 134.01 | 117.44 | 123.71 | 146.71 |
| mg/L/copy | 235 | 135 | 169 | 177 |

Figure 6:
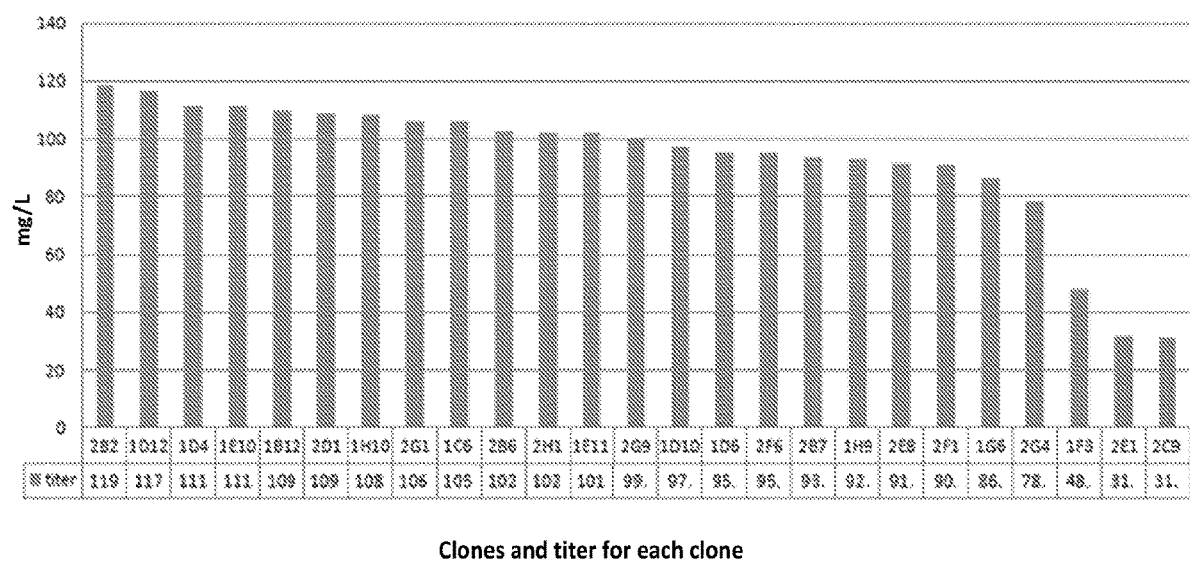
FIG. 6 is a graph showing the expression titer (mg/L) of individual clones of DXB11 cells with a Herceptin gene inserted at a Siva1 site.
Figure 7:
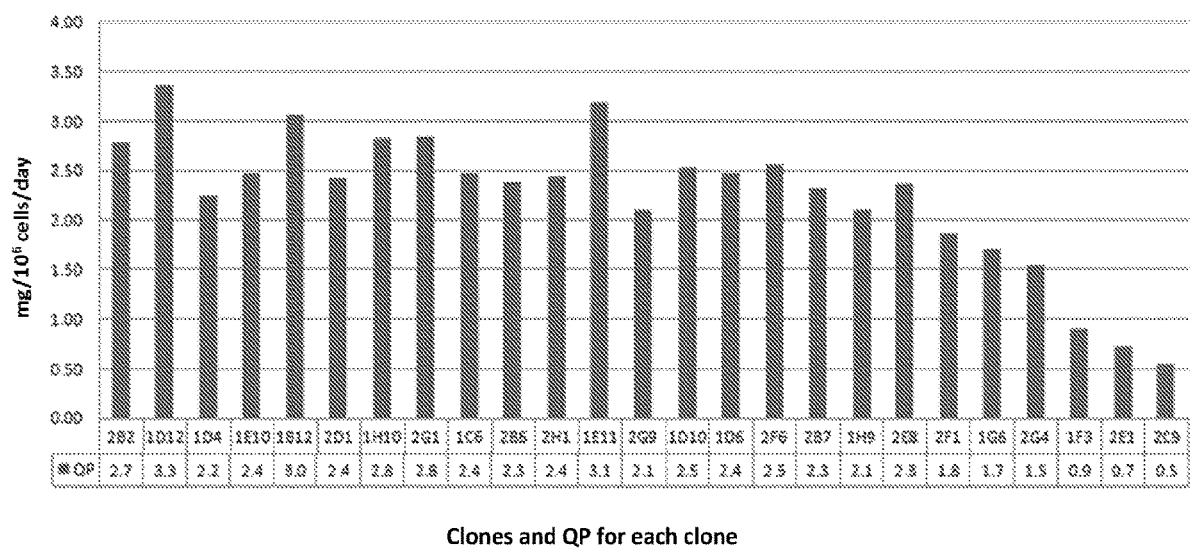
FIG. 7 is a graph showing the specific productivity (QP; mg/$10^6$ cells/day) of individual clones of DXB11 cells with a Herceptin gene inserted at a Siva1 site.

Individual clones from the Siva1 pool were also tested. As shown in FIGS. 6 and 7, these clones all exhibited increased expression of the Herceptin gene. Analysis showed that, among these clones, although some had off-target insertions and some had multiple copies of the insertions, many had only one copy of an on-target insertion.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

What is claimed is:

1. An engineered Chinese hamster ovary (CHO) cell, comprising an exogenous nucleic acid molecule inserted in the genome of the engineered cell, wherein the engineered cell is obtained by a process that includes introducing into a CHO host cell a construct for inserting the exogenous nucleic acid molecule into a target site within an expression-enhancing sequence in the genome of the host cell, the expression-enhancing sequence being at least 8000 identical to a sequence selected from SEQ ID NOs: 1-16 or a 100 to 2000 nucleotide fragment thereof.

2. The engineered cell of claim 1, wherein the construct is a homology recombination construct that includes the exogenous nucleic acid molecule flanked by a first homology arm and a second homology arm, the first homology arm being homologous to a sequence upstream of the target site and the second homology arm being homologous to a sequence downstream of the target site.

3. The engineered cell of claim 2, wherein the expression-enhancing sequence is selected from SEQ ID NOs: 1-16.

4. The engineered cell of claim 3, wherein the expression-enhancing sequence is selected from SEQ ID NOs: 2, 4, 6, 8, 10, 12, 14, and 16.

5. The engineered cell of claim 1, wherein the engineered cell contains the exogenous nucleic acid molecule at the target site.

6. The engineered cell of claim 5, wherein the expression-enhancing sequence is SEQ ID NO: 7 or 9.

7. The engineered cell of claim 5, wherein the expression-enhancing sequence is SEQ ID NO: 8 or 10.

8. The engineered cell of claim 1, wherein the engineered cell contains the exogenous nucleic acid molecule at an off-target site, wherein the engineered cell expresses a higher level of the exogenous nucleic acid molecule as compared to a control cell.

9. The engineered cell of claim 1, wherein the exogenous nucleic acid molecule encodes a polypeptide.

10. A method of producing an engineered Chinese hamster ovary (CHO) cell that contains an exogenous nucleic acid molecule, comprising introducing into a host CHO cell a construct for inserting the exogenous nucleic acid molecule into a target site within an expression-enhancing sequence in the genome of the host cell, the expression-enhancing sequence being at least 80% identical to a sequence selected from SEQ ID NOs: 1-16 or a 100 to 2000 nucleotide fragment thereof, whereby the exogenous nucleic acid is inserted into a genomic site in the host cell to produce the engineered cell.

11. The method of claim 10, wherein the construct is a homology recombination construct that includes the exogenous nucleic acid molecule flanked by a first homology arm and a second homology arm, the first homology arm being homologous to a sequence upstream of the target site and the second homology arm being homologous to a sequence downstream of the target site.

12. The method of claim 11, wherein the expression-enhancing sequence is selected from SEQ ID NOs: 1-16.

13. The method of claim 11, wherein the expression-enhancing sequence is selected from SEQ ID NOs: 2, 4, 6, 8, 10, 12, 14, and 16.

14. The method of claim 11, wherein the expression-enhancing sequence is SEQ ID NO: 7 or 9.

15. The method of claim 11, wherein the expression-enhancing sequence is SEQ ID NO: 8 or 10.

16. The method of claim 10, further comprising, after the introducing step, selecting an engineered CHO cell that expresses a higher level of the exogenous nucleic acid molecule as compared to a control CHO cell.

17. The method of claim 10, wherein the exogenous nucleic acid molecule encodes a polypeptide.

18. A construct for inserting an exogenous nucleic acid molecule into a target site within an expression-enhancing sequence in the genome of a Chinese Hamster ovary (CHO) host cell, the expression-enhancing sequence being at least 80% identical to a sequence selected from SEQ ID NOs: 1-16 or a 100 to 2,000 nucleotide fragment thereof.

19. The construct of claim 18, wherein the construct is a homology recombination construct including a first homology arm that is homologous to a sequence upstream of the target site and a second homology arm that is homologous to a sequence downstream of the target site.

20. The construct of claim 19, wherein the expression-enhancing sequence is selected from SEQ ID NOs: 1-16.

21. The construct of claim 20, wherein the expression-enhancing sequence is selected from SEQ ID NOs: 2, 4, 6, 8, 10, 12, 14, and 16.

22. The construct of claim 20, wherein the expression-enhancing sequence is SEQ ID NO: 7 or 9.

23. The construct of claim 20, wherein the expression-enhancing sequence is SEQ ID NO: 8 or 10.

24. The construct of claim 19, further comprising an exogenous nucleic acid molecule flanked by the first homology arm and the second homology arm.

25. The construct of claim 24, further comprising a promoter operable linked to the exogenous nucleic acid molecule.

\* \* \* \* \*